United States Patent [19]

Rorer

[11] Patent Number: 4,589,909

[45] Date of Patent: May 20, 1986

[54] BENZOFURAN AND BENZOTHIOPHENE SULFONAMIDES

[75] Inventor: Morris P. Rorer, Newark, Del.

[73] Assignee: E. I. Du Pont de Nemours and Company, Wilmington, Del.

[21] Appl. No.: 706,961

[22] Filed: Mar. 6, 1985

Related U.S. Application Data

[63] Continuation-in-part of Ser. No. 617,608, Jun. 5, 1984, abandoned.

[51] Int. Cl.[4] .................. C07D 251/18; C07D 251/16; A01N 43/68; A01N 43/66
[52] U.S. Cl. ............................................. 71/90; 71/93; 71/92; 544/207; 544/212; 544/321; 544/323; 544/324; 544/331; 544/332
[58] Field of Search .................... 544/207, 212; 71/93, 71/90

[56] References Cited

U.S. PATENT DOCUMENTS

| 4,391,627 | 7/1983 | Levitt | 544/212 |
| 4,494,979 | 1/1985 | Rorer | 544/212 |
| 4,514,211 | 4/1985 | Rorer | 544/212 |

FOREIGN PATENT DOCUMENTS

| 837434 | 10/1983 | South Africa . | |
| 2081712 | 2/1982 | United Kingdom | 544/212 |

*Primary Examiner*—John M. Ford

[57] ABSTRACT

Benzofuran and benzothiophene sulfonamides show utility as herbicides and plant growth regulants.

30 Claims, No Drawings

BENZOFURAN AND BENZOTHIOPHENE SULFONAMIDES

RELATED APPLICATIONS

This application is a continuation-in-part of my co-pending application, U.S. Ser. No. 617,608, filed June 5, 1984 now abandoned.

BACKGROUND OF THE INVENTION

This invention relates to benzofuran and benzothiophene sulfonamides which are novel. The compounds of this invention and their agriculturally suitable salts, are useful as agricultural chemicals, e.g., plant growth regulants and herbicides. The invention also includes intermediates useful for making these compounds.

Netherlands Patent No. 121,788, published Sept. 15, 1966, discloses the preparation of compounds of the following Formula and their use as general or selective herbicides:

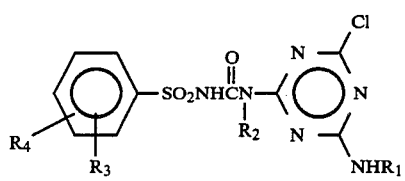

(i)

wherein
  $R_1$ and $R_2$ may independently be alkyl of 1-4 carbon atoms; and
  $R_3$ and $R_4$ may independently be hydrogen, chlorine or alkyl of 1-4 carbon atoms.

U.S. Pat. No. 3,637,366 discloses compounds having the formula:

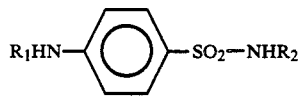

wherein
  $R_1$ is hydrogen or lower saturated aliphatic acyl and
  $R_2$ is hydrogen, 2-pyrimidinyl, pyridyl, amidino, acetyl or carbamoyl.

The disclosed compounds are said to provide control of crabgrass, cress, endive, clover and *Poa annua*.

French Patent No. 1,468,747 discloses the following para-substituted phenylsulfonamides as being useful as antidiabetic agents:

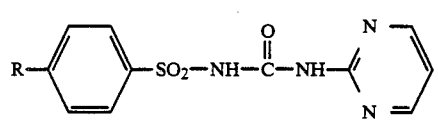

wherein R=H, halogen, $CF_3$ or alkyl.

Logemann et al., Chem. Ab., 53, 18052g (1959), disclose a number of sulfonamides, including uracil derivatives and those having the formula:

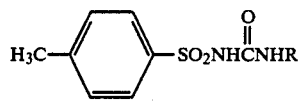

wherein
  R is butyl, phenyl or

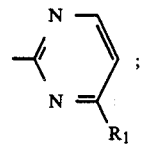

and
  $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

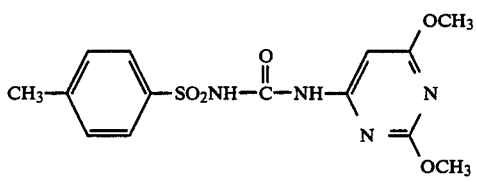

U.S. Pat. No. 4,127,405 teaches compounds which are useful for controlling weeds in wheat having the formula

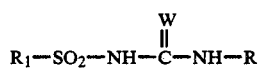

wherein
  R is

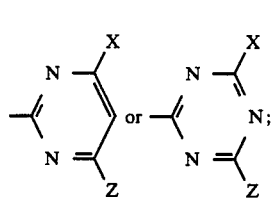

$R_1$ is

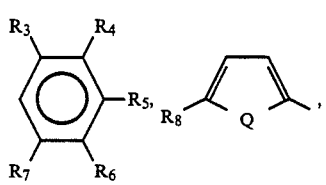

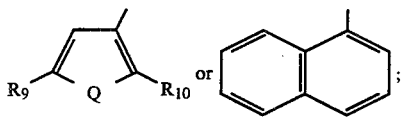

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Z is methyl or methoxy;

or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In addition, unexamined European Patent Application No. 35,893 teaches o-alkylsulfonylbenzenesulfonylureas which are useful as herbicides.

In U.S. Pat. No. 4,391,627, there is a disclosure of herbicidal benzo[b]thiophene- and benzofuransulfonylureas in which the sulfonylureido group is bonded to the heterocyclic ring.

South African Patent Application No. 835165 discloses herbicidal sulfonylureas of the general structure shown below:

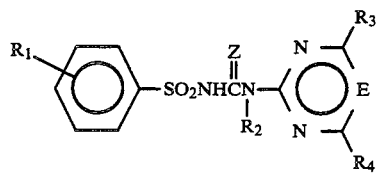

A wherein A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or $SO_2$— group.

South African Patent Application No. 837,434 discloses herbicidal sulfonamides of formula

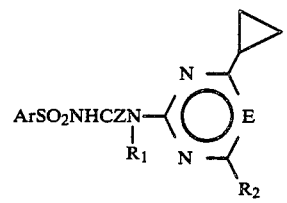

where Ar is

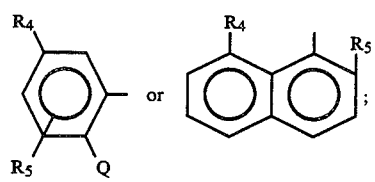

and $R_2$ is halogen, $C_1$–$C_3$ alkyl, $C_1$–$C_3$ haloalkyl, $C_1$–$C_3$ alkoxy, $C_1$–$C_3$ haloalkoxy, amino, $C_1$–$C_3$ alkylamino, di($C_1$–$C_3$ alkyl)amino, $C_3$–$C_6$ cycloalkyl or $C_2$–$C_6$ alkoxyalkyl.

Unexamined European Patent Application 79,683, published May 25, 1983, discloses herbicidal sulfonamides of formula

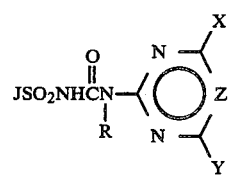

where

J is various benzofuran, benzothiophene, 1-benzopyran, 1-benzothiopyran, 1-benzoxepin and 1-benzothiopin moieties;

X is H, $CH_3$, $OCH_3$ or Cl;

Y is $CH_3$, $OCH_3$, $OCH_2CH_3$, $CH_2OCH_3$, $CH_2CH_3$, $NH_2$, $NHCH_3$ or $N(CH_3)_2$; and Z is CH or N.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Prevention or minimizing the loss of a portion of such valuable crops by killing, or inhibiting the growth of undesired vegetation is one way of improving this efficiency. A wide variety of materials useful for killing, or inhibiting (controlling) the growth of undesired vegetation is available; such materials are commonly referred to as herbicides. The need still exists however, for more effective herbicides.

SUMMARY OF THE INVENTION

This invention relates to compounds of Formula I, Formula I', Formula II and Formula II' and their agriculturally suitable salts, suitable agricultural compositions containing them, and their use as pre-emergence and/or post-emergence herbicides.

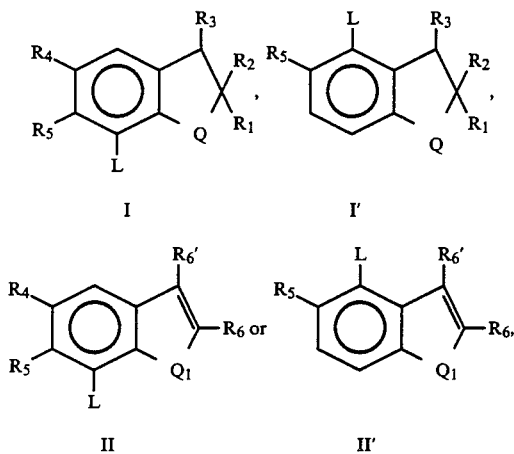

I  I'

II  II' wherein
Q is O, S, SO or $SO_2$;
$Q_1$ is O, S or $SO_2$;
L is

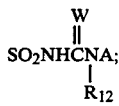

$R_1$ is H or $C_1$-$C_4$ alkyl;
$R_2$ is H or $C_1$-$C_4$ alkyl;
$R_3$ is H or $CH_3$;
$R_4$ is H, Cl, $CH_3$, $CF_3$, $OCH_3$, Br, F, $SCH_3$ or $OCF_2H$;
$R_5$ is H, $CH_3$, $OCH_3$, Cl, Br, $NO_2$, $CO_2R_7$, $SO_2R_8$, $OSO_2R_9$, $SO_2NR_{10}R_{11}$, F, $CF_3$, $SCH_3$, $OCF_2H$ or $SO_2N(OCH_3)CH_3$;
$R_6$ is H, Cl, Br or $C_1$-$C_4$ alkyl;
$R_6'$ is H, $CH_3$, Cl or Br;
$R_7$ is $C_1$-$C_3$ alkyl, $CH_2CH=CH_2$, $CH_2CH_2OCH_3$ or $CH_2CH_2Cl$;
$R_8$ is $C_1$-$C_3$ alkyl;
$R_9$ is $C_1$-$C_3$ alkyl or $CF_3$;
$R_{10}$ and $R_{11}$ are independently $C_1$-$C_2$ alkyl;
$R_{12}$ is H or $CH_3$;
W is O or S;
A is

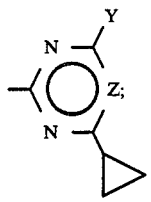

Y is $C_1$-$C_2$ alkyl, $C_1$-$C_2$ alkoxy, $C_1$-$C_2$ alkoxymethyl, $OCF_2H$, $SCF_2H$, $OCH_2CF_3$, $OCH_2CH_2F$, $CF_3$, $OCH_2CH=CH_2$, $OCH_2C\equiv CH$, $NHCH_3$, $N(CH_3)_2$ or $CH(OCH_3)_2$; and
Z is CH or N;
and their agriculturally suitable salts; provided that
(1) in Formulae II and II', when $R_5$ is $NO_2$, then $R_6$ is $C_1$-$C_4$ alkyl and $R_6'$ is $CH_3$;
(2) when Q is SO, then W is O;
(3) when $R_4$ is other than H, then $R_5$ is H;
(4) $R_1$ and $R_2$ taken together are not more than four carbon atoms; and
(5) when Y is $OCF_2H$, then Z is CH.

Preferred for reasons of their higher herbicidal activity or more favorable ease of synthesis are:
(1) Compounds of the generic scope of Formula I where W is O.
(2) Compounds of Preferred 1 where $R_5$ is H, F, Cl, $CH_3$, $OCH_3$, $CO_2(C_1$-$C_2$ alkyl), or $SO_2(C_1$-$C_2$ alkyl), $R_4$ is H, Cl, $CH_3$ or $OCH_3$, Y is $CH_3$, $OCH_3$, $OC_2H_5$, $CH_2OCH_3$, $CH(OCH_3)_2$, $CF_3CH_2O$ or $OCF_2H$ and $R_{12}$ is H.
(3) Compounds of Preferred 2 where $R_3$ and $R_4$ are H, $R_1$ is H, $CH_3$ or $CH_2CH_3$, $R_2$ is H or $CH_3$, and $R_5$ is H, F, Cl, $CH_3$ or $OCH_3$.
(4) Compounds of Preferred 3 where Y is $CH_3$, $OCH_3$ or $CH_2OCH_3$.
(5) Compounds of the generic scope of Formula II where W is O.
(6) Compounds of Preferred 5 where $R_6$ is H, $CH_3$ or $CH_2CH_3$ and $R_6'$ is H.
(7) Compounds of Preferred 6 where $R_5$ is H, Cl, $CH_3$, $OCH_3$, $CO_2(C_1$-$C_2$ alkyl) or $SO_2(C_1$-$C_2$ alkyl), $R_4$ is H, Cl, $CH_3$ or $OCH_3$, Y is $CH_3$, $OCH_3$, $OC_2H_5$, $CH_2OCH_3$, $CH(OCH_3)_2$, $CF_3CH_2O$ or $OCF_2H$ and $R_{12}$ is H.
(8) Compounds of Preferred 7 where $R_4$ and $R_6'$ are H, $R_5$ is H, Cl, F, $CH_3$ or $OCH_3$ and, $R_6$ is H or $CH_3$.
(9) Compounds of Preferred 8 where Y is $CH_3$, $OCH_3$ or $CH_2OCH_3$.

DETAILED DESCRIPTION OF THE INVENTION

Synthesis

As shown in Equations 1 and 2, the compounds of Formulae (I), (I'), (II) and (II') can be prepared by reacting sulfonylisocyanates or isothiocyanates of Formulae (III) and (IV), with an appropriate amine of Formula (V), wherein $R_1$ to $R_6'$, $R_{12}$, A, $Q_1$, Q and W are as previously defined.

Equation 1

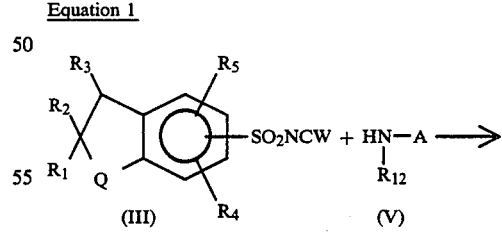

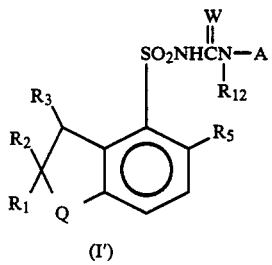

-continued (III) + (V) ⟶ 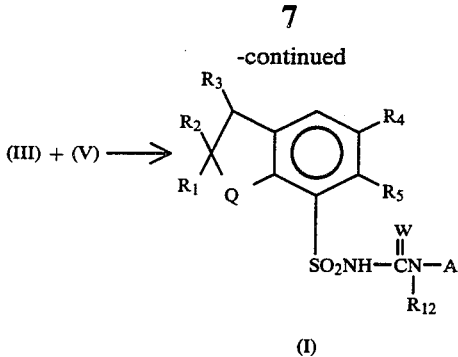

(I)

Equation 2

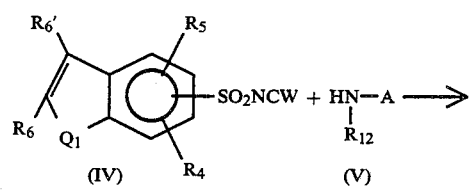

(IV)    (V)

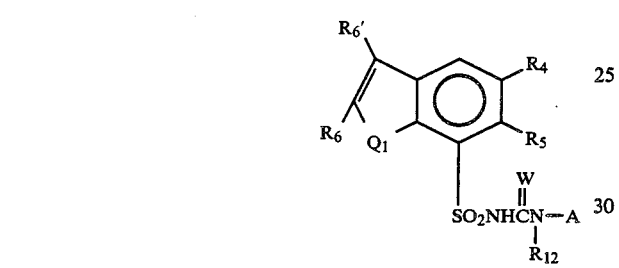

(II)

(IV) + (V) ⟶ 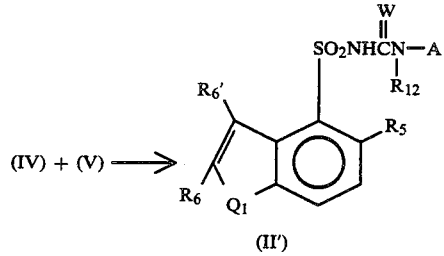

(II')

The reactions of Equations 1 and 2 are best carried out in inert aprotic organic solvents such as methylene chloride, tetrahydrofuran or acetonitrile at ambient pressure and temperature. The mode of addition is not critical; however, it is often convenient to add the sulfonylisocyanate or isothiocyanate to a stirred suspension of amine V. The reactions are generally exothermic. In some cases the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, ethyl acetate or pentane, and filtration.

Alternatively, as shown in Equations 3 and 4, compounds I, I', II and II', where $R_5$ is other than $CO_2R_7$ and W=O, can be prepared by reacting arylsulfonamides of Formulae (VI) and (VII), respectively, with an appropriate methyl carbamate of Formula (VIII), in the presence of an equimolar amount of trimethylaluminum.

Equation 3

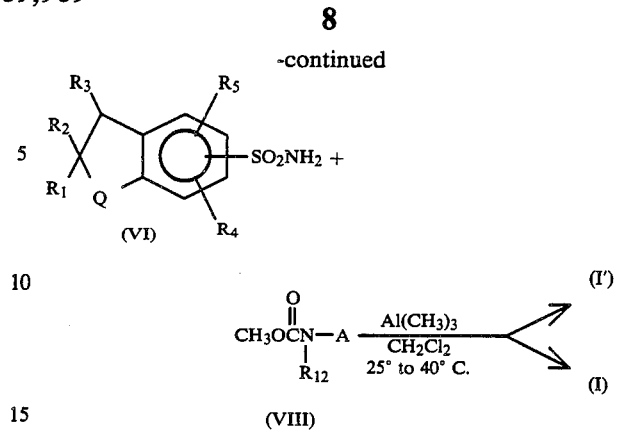

Equation 4

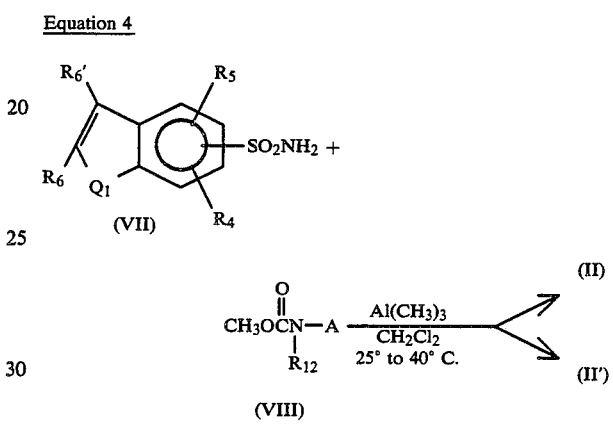

wherein for Equations 3 and 4 $R_1$ to $R_6'$, $R_{12}$, A, $Q_1$ and Q are as previously defined, except $R_5$ is other than $CO_2R_7$.

The reactions of Equations 3 and 4 are best carried out in methylene chloride at about 25° to 40° C. for 10 to 96 hours under a nitrogen atmosphere. The product is isolated by addition of an aqueous acetic acid or hydrochloric acid solution followed by extraction of the product into methylene chloride, or by direct filtration of a product of low solubility. The product is purified by trituration with solvents such as 1-chlorobutane, ethyl acetate or ethyl ether or subjected to chromatography procedures. Trimethylaluminum is commercially available. The reactions of Equations 3 and 4 are particularly useful for preparing I, I', II and II' (W=O) where sulfonylisocyanates are difficult to prepare from the corresponding sulfonamides VI and VII.

The compounds of Formulae (I), (I'), (II) and (II') where $R_{12}$ is H and W is O can also be prepared, as shown in Equation 3a and 4a by contacting a sulfonamide of Formula VI or Formula VII with a heterocyclic phenyl carbamate of Formula VIII' in the presence of equimolar amount of a tertiary amine such as 1,5-diazabicyclo[5,4,0]undec-5-ene (DBU).

Equation 3a

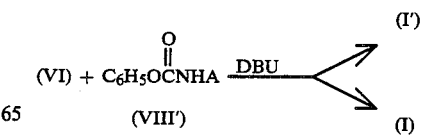

Equation 4a

-continued

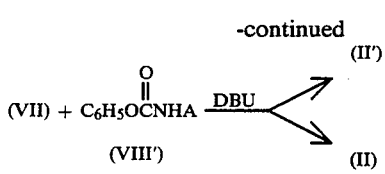

where in Equations 3a and 4a, $R_1$ to $R_6'$, A $Q_1$ and $Q_2$ are as previously defined.

The reactions of Equations 3a and 4a are best carried out by adding DBU to a mixture of the sulfonamide (VI) or (VII) and the phenyl carbamate (VIII') in a solvent such as dioxane or acetonitrile at or about ambient temperatures. After a period of about 0.5 to 24 hours, the reaction mixture is diluted with water and acidified with aqueous hydrochloric acid and/or aqueous acetic acid. The product can be isolated by filtration of extraction into an organic solvent, then purified by methods previously described.

The phenyl carbamates of Formula (VIII') can be prepared by the reaction of the heterocyclic amine of Formula V, where $R_{12}$ is H, with phenyl carbonate or phenyl chloroformate in the presence of a suitable base such as sodium hydride or pyridine.

In addition, as shown in Equations 3b and 4b below, compounds of Formulae (I), (I'), (II) and (II') (where W=O) can be prepared by reacting sulfonylcarbamates VI' and VII', respectively, with an appropriate amine V.

Equation 3b

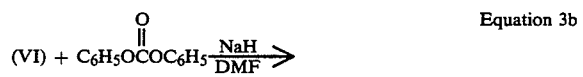

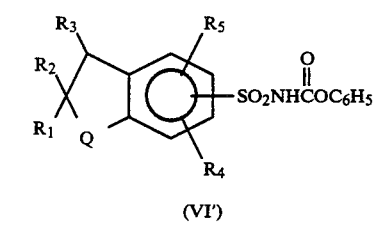

(VI')

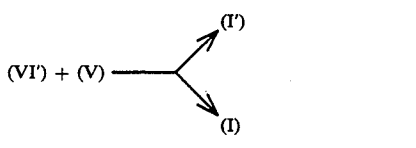

Equation 4b

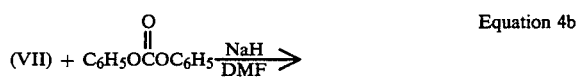

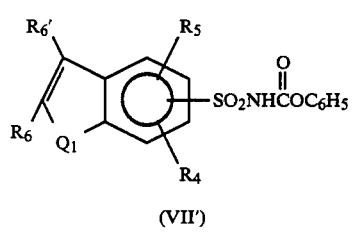

(VII')

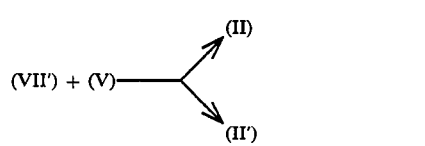

wherein for Equations 3b and 4b $R_1$ to $R_6'$, $R_{12}$, A, $Q_1$ and Q are as previously defined, except $R_5$ is other than $CO_2R_7$.

The reactions are run at 50°–100° C. in a solvent such as dioxane for 0.5 to 24 hours as taught in EPO Publication No. 44807. The required carbamates VI' and VII' are prepared by reacting corresponding sulfonamides VI and VII, respectively, with diphenylcarbonate in the presence of a strong base.

The intermediate sulfonylisocyanates of Formulae (III) and (IV) (W=O) in Equations 1 and 2 can be prepared from sulfonamides by methods taught in U.S. Pat. No. 4,238,621. The method requires reacting sulfonamides with phosgene, in the presence of n-butylisocyanate and a tertiary amine catalyst, at reflux in a solvent such as xylene or chlorobenzene. A preferred catalyst is 1,4-diazabicyclo[2.2.2]octane (DABCO).

Alternatively, the sulfonylisocyanates can be prepared from sulfonamides by a two-step procedure. This involves (a) reacting the sulfonamides with n-butylisocyanate and a base such as $K_2CO_3$ at reflux in an inert solvent such as 2-butanone to form a n-butyl sulfonylurea; and (b) reacting this compound with phosgene and DABCO catalyst at reflux in xylene or chlorobenzene solvent. The latter method is similar to a procedure taught by Ulrich and Sayigh, *New Methods of Preparative Organic Chemistry*, Vol. VI, p. 223–241, Academic Press, New York and London, W. Foerst Ed.

The intermediate sulfonylisothiocyanates of Formulae (III) and (IV) (W=S) in Equations 1 and 2 can be prepared from sulfonamides by methods taught in H. Hartke, *Arch. Pharm.*, 229, 174 (1966). The method requires (a) reacting an appropriate sulfonamide with an equivalent amount of carbon disulfide and two equivalents of potassium hydroxide in dimethylformamide at room temperature for 1–8 hours to form the dipotassium salt of the sulfonyliminodithiocarbonate; (b) diluting the suspension with ethyl acetate, ethyl ether or similar aprotic solvent to cause the salt to precipitate, (c) reacting the isolated, dried salt with phosgene in an inert solvent such as xylenes, benzene, carbon tetrachloride or methylene chloride at about room temperature for 1–3 hours; and (d) isolating the sulfonylisothiocyanate, which is usually soluble in the solvent, by filtering off the insoluble potassium chloride and concentrating the filtrate. In place of phosgene, a chloroformic ester (e.g., methyl chloroformate), phosphorus pentachloride, sulfuryl chloride or thionyl chloride may be used.

The compounds of Formula (I), (I'), (II) and (II'), where W is S and $R_{12}$ is H, may also be prepared by reacting an appropriate sulfonamide with a heterocyclic isothiocyanate of Formula (V'), as shown in Equation 4b.

Equation 4b

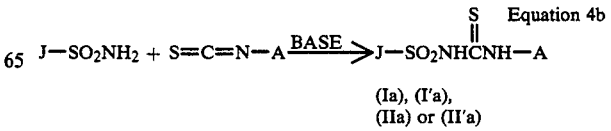

(Ia), (I'a),
(IIa) or (II'a)

-continued

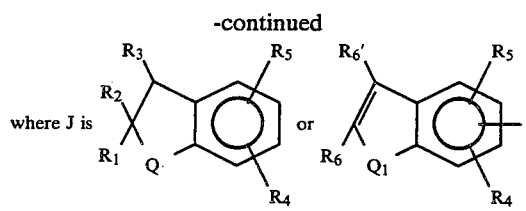

where J is and wherein $R_1$ to $R_6'$, Q, $Q_1$ and A are as originally defined.

The reaction is carried out at 25° to 80° C. in an inert, aprotic solvent such as acetone or acetonitrile in the presence of a base such as potassium carbonate for 0.5 to 24 hours. The required heterocyclic isothiocyanates V' are prepared from the corresponding amines V as taught in EPO Publication 35893.

The intermediate sulfonamides of Formulae (VI) and (VII) in Equations 3 and 4 can be prepared by reacting corresponding sulfonyl chlorides with ammonium hydroxide or ammonia in an inert solvent such as tetrahydrofuran or methylene chloride at ambient temperature, according to procedures widely reported in the literature for preparing other sulfonamides, e.g., Crossley et al., *J. Am. Chem. Soc.*, 60, 2223 (1938) and Pailer, *Monatsh*, 92, 677 (1961).

Arylsulfonyl chlorides are ordinarily prepared from aromatic amines by diazotization with sodium nitrite in HCl, followed by reaction of the diazonium salt with sulfur dioxide and cupric chloride in acetic acid, according to the teachings of Yale and Sowinski, *J. Org. Chem.*, 25, 1824 (1960). As shown in Equations 5 and 6, however, sulfonyl chlorides (XI) and (XII) are preferably prepared by a modification of this procedure.

Equation 5

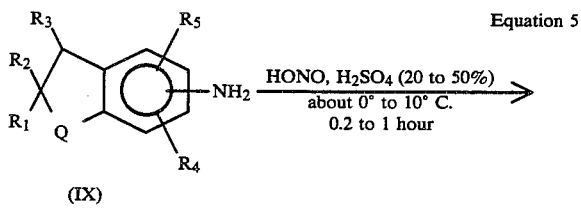

(IX)

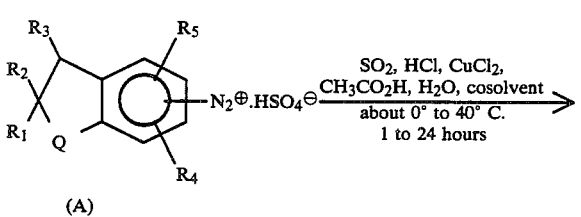

(A)

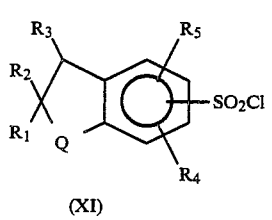

(XI)

-continued

Equation 6

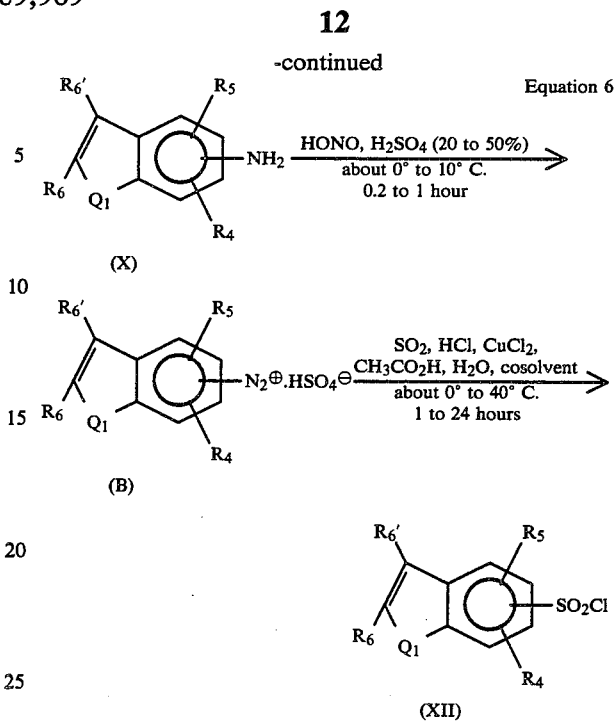

The diazotization reactions of Equations 5 and 6 are best carried out with sodium nitrite in dilute sulfuric acid (about 20 to 50%), at about 0° to 10° C. for about 0.2 to 1 hour. This method for preparing diazonium salts from benzofuranamines and benzo[b]thiopheneamines is widely reported in the literature, e.g., Bordwell and Stange, *J. Am. Chem. Soc.*, 27, 5939 (1955); Arnold and McCool, ibid 64, 1315 (1942); Neth. Appl. No. 6,602,601; and U.S. Pat. No. 4,032,649.

The sulfonyl chlorides in Equations 5 and 6 are prepared by reacting the diazonium salts with stirred suspensions containing sulfur dioxide, hydrochloric acid and cupric chloride. The reactions are preferably carried out in a cosolvent mixture consisting of acetic acid-water (about 1:1) and an immiscible, inert solvent such as 1-chlorobutane or methylene chloride, preferably 1-chlorobutane. The reactions are run at about 0° to 40° C., preferably at 25° to 40° C. for 1 to about 24 hours. The mode of addition is not critical; it is however, often convenient to add the diazonium salt to the suspension containing in sulfur dioxide. The sulfonyl chlorides are isolated by addition of water, separation of the organic phase, washing the organic phase with saturated aqueous NaHCO$_3$ and water and evaporation of the solvent under reduced pressure at less than about 50° C.

An alternate method for preparing some 2,3-dihydro-7-benzo[b]thiophenesulfonamides of Formula (VI) (Q=S) in Equation 3 above is shown in Equation 7 below.

Equation 7

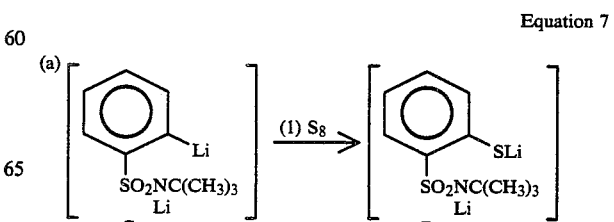

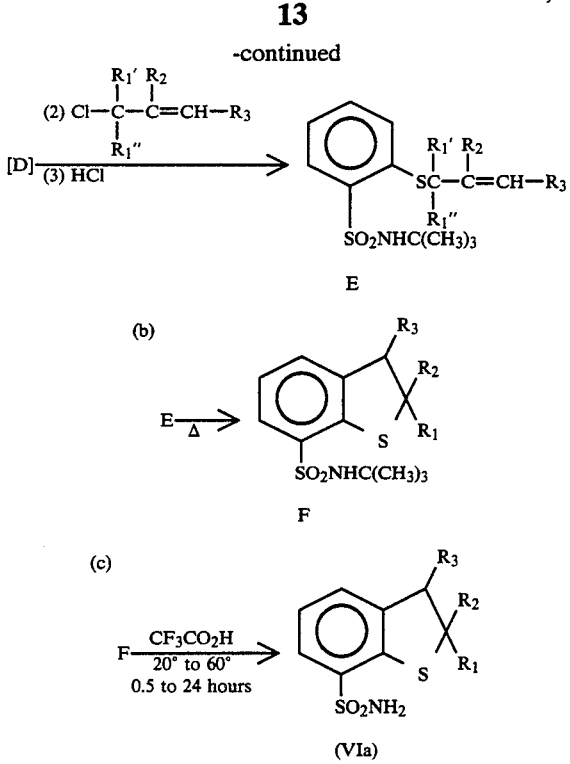

wherein
- $R_1$ is $C_1$–$C_4$ alkyl;
- $R_2$ and $R_3$ are as previously defined;
- $R_1'$ is H or $CH_3$; and
- $R_1''$ is H or $C_1$–$C_3$ alkyl; when $R_1''$ is $C_3H_7$, $R_1'$ is H.

The reactions of Equation 7(a) are run in-situ as follows: The dilithium salt C is prepared by reacting t-butylbenzenesulfonamide with two equivalents of n-butyl lithium at 0° to 30° C. in an inert solvent such as tetrahydrofuran for one to five hours, according to the teachings of Lombardino, *J. Org. Chem.*, 36, 1843 (1971). The N-t-butyl-2-propenylthiobenzenesulfonamide of Formula E is then prepared by (1) contacting this mixture containing C with elemental sulfur at 0° and stirring at ambient temperature for one to five hours to form lithium thiolate D; (2) contacting this mixture with an appropriate allyl halide at 0° and stirring at ambient temperature for about 24 hours to form E; and (3) isolating E by addition of dilute hydrochloric acid to this mixture to decompose any salts present, followed by separation and concentration of the organic phase. The reaction of organolithium reagents with sulfur to form lithium thiolates which may be alkylated in-situ is known in the art, e.g., Gschwend et al., "Organic Reactions", 26, Chapter 1, p. 83 (1979) and references cited therein.

In Reaction 7(b) above, the N-t-butyl-2,3-dihydro-7-benzo[b]thiophenesulfonamides of Formula F are prepared by heating E either neat or in an inert solvent such as quinoline or N,N-dimethylaniline at 150°–300° C. for 0.25 to 2 hours to cause cyclization. Compound F is isolated by addition of an inert solvent such as ether or methylene chloride, washing well with dilute hydrochloric acid and water, followed by separation and concentration of the organic phase. Compound F can be purified by column chromatography and recrystallization procedures.

And in Reaction 7(c), the t-butylsulfonamides F are dealkylated to form sulfonamides VIa by reacting F with excess trifluoroacetic acid at 20° to 40° C. for about 10 to 30 hours. Compounds VIa are isolated and purified by concentration of the reaction mixture, addition of methylene chloride to the residue, washing the suspension with dilute aqueous $NaHCO_3$ and concentration of the organic phase. Alternatively, t-butylsulfonamides F may be converted to sulfonamides VIa by heating in methanol containing at least an equimolar quantity of hydrochloric acid, followed by concentration of the reaction mixture and precipitation of the product with ether.

The amines of Formulae (IX) and (X) in Equations 5 and 6 above are important starting materials for the preparation of the compounds of this invention, and can be prepared according to the teachings of unexamined European Patent Application No. 79,683 (published May 25, 1983) by those skilled in the art.

The cyclopropyl-pyrimidines and triazines of Formula (V) in Equations 1 and 2 can also be prepared by known methods, or simple modifications thereof, by those skilled in the art. For details, see, for example, South African Patent Application No. 837,434 (published Oct. 5, 1983) which describes methods for the synthesis of cyclopropylpyrimidines and triazines substituted by such groups as halogen, alkyl, haloalkyl, alkoxy, haloalkoxy, amino, alkylamino, dialkylamino or alkyoxyalkyl. See also, for example, unexamined European Patent Application No. 84,224, published July 27, 1983, which describes the synthesis of pyrimidine- and triazineamines substituted by such groups as dialkoxymethyl or 1,3-dioxolan-2-yl. See also, for example, South African Patent Application Nos. 825,045 and 825,671 which describe the synthesis of aminopyrimidines or triazines substituted by such groups as haloalkoxy or haloalkylthio groups, e.g., $OCH_2CH_2Cl$, $OCH_2CF_3$, $OCF_2H$ or $SCF_2H$.

For the general synthesis of aminopyrimidines and triazines, see also, for example, the following publications:

"The Chemistry of Heterocyclic Compounds", a series published by Interscience Publishers, Inc., New York and London;

"Pyrimidines", Vol. 16 of the above series by D. J. Brown;

"S-Triazines and Derivatives", Vol. 13 of the same series by E. M. Smolin and L. Rappaport; and F. C. Schaefer, U.S. Pat. No. 3,154,547; and K. R. Huffman and F. C. Schaefer, *J. Org. Chem.*, 28, 1812 (1963).

Agriculturally suitable salts of compounds of Formulae (I), (I'), (II) and (II') are also useful herbicides and can be prepared by a number of ways known to the art. For example, metal salts can be made by treating compounds of Formulae (I), (I'), (II) or (II') with a solution of alkali or alkaline earth metal salt having a sufficiently basic anion (e.g., hydroxide, alkoxide, carbonate or hydride). Quaternary amine salts can be made by similar techniques.

Salts of compounds of Formulae (I), (I'), (II) and (II') can also be prepared by exchange of one cation to another. Cationic exchange can be effected by direct treatment of an aqueous solution of a salt of a compound of Formulae (I), (I'), (II) or (II') (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formulae (I), (I'), (II) or (II') (e.g., an alkali metal or quaternary amine salt) through a column packed with a cation exchanged resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formulae (I), (I'), (II) or (II') with a suitable acid, e.g. p-toluenesulfonic acid, trichloroacetic acid or the like.

In the following examples all parts are by weight and temperature in °C. unless otherwise indicated.

EXAMPLE 1

2,3-Dihydro-2,2-dimethyl-7-benzofuransulfonyl chloride

A diazonium salt was prepared by adding 13.8 g of sodium nitrite to a suspension of 32.6 g of 7-amino-2,3-dihydro-2,2-dimethylbenzofuran and 40 ml of concentrated sulfuric acid in 200 ml water cooled 0° to 5° C. After stirring for about 0.4 hour at 0° to 5° C., the diazonium salt suspension was poured in one portion into a mixture consisting of 170 ml of acetic acid, 40 ml of concentrated hydrochloric acid, 17 g of cupric chloride dihydrate and 30 ml of sulfur dioxide and cooled by 10° C. by an ice-water bath. The mixture was stirred about 1 hour at 15° to 25° C. Then 400 ml of 1-chlorobutane and 200 ml of water was added and the mixture was stirred and heated at 35° C. for 5 hours. After cooling to room temperature, the organic layer was separated, washed with saturated aqueous NaHCO$_3$ and water, and dried over sodium sulfate for 0.5 hour. The solvent was evaporated under reduced pressure at less than 45° C. to give 26 g of crude 2,3-dihydro-2,2-dimethyl-7-benzofuransulfonyl chloride as an oil.

EXAMPLE 2

2,3-Dihydro-2,2-dimethyl-7-benzofuransulfonamide

A solution of 26 g of 2,3-dihydro-2,2-dimethyl-7-benzofuransulfonyl chloride prepared in Example 1, in 130 ml of tetrahydrofuran, was cooled in an ice-water bath while about 30 ml of concentrated aqueous ammonium hydroxide was added portionwise at 10° to 30° C. The resulting suspension was stirred at room temperature for 3 hours, then the solvent was evaporated under reduced pressure. The residue was stirred in 150 ml of water for 0.5 hour, then filtered. The crude, wet solid was dissolved in chloroform and dried over sodium sulfate. The solvent was evaporated under reduced pressure to give a dry solid. The solid was washed once with about 100 ml of hot toluene to give 20 g of 2,3-dihydro-2,2-dimethyl-7-benzofuransulfonamide, m.p. 163°-165° C.

Anal. Calcd. for $C_{10}H_{13}NO_3S$: C, 52.8; H, 5.8; N, 6.2; Found: C, 52.5; H, 5.7; N, 6.1.

EXAMPLE 3

N-(Butylaminocarbonyl)-2,3-dihydro-2,2-dimethyl-7-benzofuransulfonamide

A solution of 19 g of 2,3-dihydro-2,2-dimethyl-7-benzofuransulfonamide prepared in Example 2 and 9.9 g of n-butyl isocyanate in 200 ml of 2-butanone was refluxed with 11.5 g of anhydrous potassium carbonate for 7 hours. The resulting mixture was concentrated to dryness in vacuo. The residue was taken up in 400 ml of water and extracted once with 100 ml of ethyl ether. The aqueous layer was acidified with 2N HCl and the resulting mixture was filtered and suction dried. The still slightly wet solid was washed once with 100 ml of hot acetonitrile, then suction dried an additional 8 hours to give 23 g of N-(butylaminocarbonyl)-2,3-dihydro-2,2-dimethyl-7-benzofuransulfonamide, m.p. 200°-203° C.

Anal. Calcd. for $C_{15}H_{22}N_2O_4S$: C, 55.2; H, 6.8; N, 8.6; Found: C, 54.8; H, 6.6; N, 8.5.

EXAMPLE 4

2,3-Dihydro-2,2-dimethyl-7-benzofuransulfonyl isocyanate

A suspension of 22 g of the N-(n-butylaminocarbonyl)-2,3-dihydro-2,2-dimethyl-7-benzofuransulfonamide prepared in Example 3, in 125 ml of xylene containing 0.3 g of DABCO was heated at 130°-135° C. while 5.3 ml of phosgene was added portionwise at a rate to maintain a reflux temperature of 130°-135° C. The mixture was refluxed for an additional 1.5 hours, cooled under nitrogen, and concentrated to dryness in vacuo. A sample of the crude oily product displayed a characteristic sulfonyl isocyanate band in the IR at 2200 cm$^{-1}$.

EXAMPLE 5

N-[(4-Cyclopropyl-6-methylpyrimidin-2-yl)amino-carbonyl]-2,3-dihydro-2,2-dimethyl-7-benzofuransulfonamide To a suspension of 0.47 g of 2-amino-4-cyclopropyl-6-methylpyrimidine in 15 ml of methylene chloride is added one g of the sulfonyl isocyanate prepared in Example 4. After stirring at room temperature overnight, the suspension is concentratd in vacuo, and the residue is triturated with 1-chlorobutane and filtered to give the subject compound.

EXAMPLE 6

Methyl(4-cyclopropyl-6-methylpyrimidin-2-yl)carbamate

To a suspension of 53.7 g of 2-amino-4-cyclopropyl-6-methylpyrimidine in 1000 ml of tetrahydrofuran is added portionwise, under a nitrogen atmosphere, 42.8 g of 50% sodium hydride while cooling the reaction flask in an ice-water bath. After stirring one hour at 25° C. 58.5 g of dimethylcarbonate is added dropwise at 5° to 25°. The suspension is stirred about 16 hours at ambient temperatures, then 80 ml of concentrated hydrocloride acid is added dropwise under a nitrogen atmosphere while maintaining a reaction temperature of 20° to 25° with external ice-bath cooling. The suspension is stirred 0.5 hour, filtered, and the filtrate is dried over sodium sulfate and concentrated in vacuo to give the subject compound.

EXAMPLE 7

7-Amino-2,3-dihydro-2-methylbenzo[b]thiophene (2-Aminophenyl)allylsulfide (80 g) was heated at 250°-280° C. for 3 hours, cooled, then subjected to spinning band distillation through a 20 cm column using a 5:1 reflux ratio. The fraction distilling at 80°-82° at 0.25 mm of mercury was collected (18.0 g) and shown by NMR spectrum analysis to be the title compound in approximately 90% purity.

NMR (CDCl$_3$)δ: 7.0–6.3 (m, 3H, ArH); 3.9 (m, 1H, CH); 3.5 (broad, 2H, NH$_2$); 3.5–2.6 (m, 2H, CH$_2$); and 1.35 (d, 3H, CH$_3$).

EXAMPLE 8

7-Acetamido-2,3-dihydro-2-methylbenzo[b]thiophene

To a solution of 18.0 g of 7-amino-2,3-dihydro-2-methylbenzo[b]thiophene (Example 7) in 100 ml of 1-chlorobutane was added a solution of 13.0 ml of acetic anhydride in 20 ml of 1-chlorobutane. After the exothermic reaction subsided, the mixture was refluxed for 0.3 hour, cooled in an ice-bath and filtered. The isolated solid was washed with 1-chlorobutane to yield 15.2 g of the title compound; m.p. 125°–127° C.

NMR (CDCl$_3$)δ: 7.8–6.7 (m, 4H, ArH+NH); 4.0 (m, 1H, CH); 3.6–2.8 (m, 2H, CH$_2$); 2.2 (s, 3H, CH$_3$); and 1.4 (d, 3H, CH$_3$).

EXAMPLE 9

7-Acetamido-2,3-dihydro-2-methylbenzo[b]thiophene-1,1-dioxide

To a solution of 24.7 g of 7-acetamido-2,3-dihydro-2-methylbenzo[b]thiophene (Example 8) in 100 ml of glacial acetic acid was added dropwise 60 ml of a 30% aqueous solution of hydrogen peroxide. The reaction temperature rose to 65° C. during the addition. The mixture was heated at 65°–75° C. for one hour, cooled to 25° C., diluted with water and extracted with methylene chloride. The extract was washed with water saturated with sodium bisulfite, dried over magnesium sulfate and concentrated in vacuo. The oily residue was crystallized from 1-chlorobutane to yield 14.3 g of the title compound as light yellow crystals; m.p. 115°–117° C.

NMR (CDCl$_3$)δ: 8.4–7.0 (m, 4H, ArH+NH); 3.8–2.7 (m, 3H, CH$_2$+CH); 2.2 (s, 3H, CH$_3$); and 1.5 (d, 3H, CH$_3$).

EXAMPLE 10

2,3-Dihydro-2-methyl-7-benzo[b]thiophenesulfonamide-1,1-dioxide

A. A solution of 18.6 g of 7-acetamido-2,3-dihydro-2-methylbenzo[b]thiophene-1,1-dioxide (Example 9) in 100 ml of concentrated hydrochloric acid was refluxed for one hour to yield a suspension containing the hydrochloride salt of 7-amino-2,3-dihydro-2-methylbenzo[b]thiophene-1,1-dioxide.

B. This suspension was diluted with 25 ml of glacial acetic acid, cooled to −5° C. and treated with a solution of 6.4 g of sodium nitrite in 10 ml of water such that the temperature did not rise above 5° C. The mixture was stirred for 0.5 hour at 0° C., then added in one portion to a suspension cooled at −7° C. and containing 50 ml of concentrated hydrochloric acid, 50 ml of glacial acetic acid, 2.0 g cupric chloride dihydrate and 10 ml of liquified sulfur dioxide. The mixture was stirred at 20° C. for two hours then diluted with excess water to yield a precipitate. The mixture was filtered and the solid residue was washed with water to yield 2-methyl-2,3-dihydro-7-benzo[b]thiophenesulfonyl chloride 1,1-dioxide as a crude solid.

C. This solid was dissolved in methylene chloride and contacted with 7 ml of liquified ammonia at −10° C. The mixture was stirred at 20° C. for 16 hours, then filtered and the solids were washed with water and ether. The wet, solid residue was suspended in benzene and refluxed under a Dean-Stark trap until no more water distilled from the suspension. The suspension was cooled and filtered to yield 11.4 g of the title compound; m.p. 167°–169° C.

NMR (CDCl$_3$+DMSO)δ: 8.1–7.5 (m, 3H, Ar); 7.1 (broad, 2H, NH$_2$); 3.8–2.5 (m, 3H, CH$_2$+CH); and 1.5 (d, 3H, CH$_3$).

IR (nujol): 3300, 3200 cm$^{-1}$ (NH$_2$).

EXAMPLE 11

N-[(4-Cyclopropyl-6-methylpyrimidin-2-yl)aminocarbonyl]-2,3-dihydro-2-methyl-7-benzothiophenesulfonamide-1,1-dioxide A suspension of 1.15 g sulfonamide prepared in Example 10 in 100 ml of dry methylene chloride is purged with nitrogen. To the slurry is added carefully 3.0 ml of a 20% toluene solution of trimethyl aluminum (Aldrich Chemicals) while cooling the flask at 10° to 30° C. After stirring for 0.2 hour, 0.94 g of the carbamate prepared in Example 6 is added in one portion, and the suspension was refluxed under nitrogen atmosphere for 24 hours. The suspension is cooled in an ice-water bath while 20 ml of 1N hydrochloric acid is slowly added. Afrer several minutes of stirring, the organic layer is separated, washed with water, then dried over magnesium sulfate and concentrated in vacuo. The residue is triturated with ethyl acetate to give the subject compound.

EXAMPLE 12

N-t-Butyl-2-(2-methyl-2-propenylthio)benzenesulfonamide

To an ice-cooled solution of 42.6 g of N-t-butylbenzenesulfonamide in 800 ml of dry tetrahydrofuran under a nitrogen atmosphere was added dropwise 262 ml of a 1.6M solution of n-butyl lithium in hexane. The mixture was stirred for 2 hours at 20° C. during which time a precipitate formed. The suspension was cooled to 0° C. and 6.4 g of elemental sulfur was added in one portion. The mixture was warmed to 20° C. and stirred for one hour, then cooled at 0° C. while 20.5 ml of methallyl chloride was added slowly. The mixture was stirred at 20° C. for 16 hours, then 100 ml of 10% hydrochloric acid was added. After stirring several minutes, the organic layer was separated, washed with water and brine, dried over magnesium sulfate and concentrated in vacuo. The residue was slurried in 20% ether in hexane for several minutes and filtered to yield 47 g of the title compound; m.p. 104°–107° C.

NMR (CDCl$_3$)δ: 8.2–7.2 (m, 4H, Ar); 5.6 (broad, 1H, NH); 4.9 (broad, 2H, vinyl); 3.7 (s, 2H, CH$_2$); 1.9 (m, 3H, CH$_3$); and 1.2 (s, 9H, t-butyl).

EXAMPLE 13

N-t-Butyl-2,3-dihydro-2,2-dimethyl-7-benzo[b]thiophenesulfonamide

A solution of 37 g of N-t-butyl-2-(2-methyl-2-propenylthio)benzenesulfonamide (Example 12) in 40 ml of quinoline was heated at 220° C. for one hour, then cooled to 25° C. and diluted with ether. The ether suspension was washed well with 10% hydrochloric acid followed by water and brine, then dried over magnesium sulfate and concentrated in vacuo. The oily residue was chromatographed on 300 g of silica gel, packed and eluted with 20% ether in hexane, to give a major band which was concentrated in vacuo to yield a solid.

The solid was slurried in 20% ether in hexane and filtered to yield 14.2 g of the title compound; m.p. 103°–105° C.

NMR (CDCl$_3$)δ: 7.9–7.0 (m, 3H, Ar); 5.0 (broad, 1H, NH); 3.15 (s, 2H, CH$_2$); 1.6 (m, 6H, CH$_3$); and 1.2 (s, 9H, t-butyl).

IR (nujol): 3200 cm$^{-1}$ (NH).

EXAMPLE 14

2,3-Dihydro-2,2-dimethyl-7-benzo[b]thiophenesulfonamide

A solution of 17.2 g of N-t-butyl-2,3-dihydro-2,2-dimethyl-7-benzo[b]thiophenesulfonamide (Example 13) in 100 ml of trifluoroacetic acid was stirred at 20° C. for 16 hours. The solution was concentrated in vacuo, 100 ml of fresh trifluoroacetic acid was added and the mixture stirred at 20° C. for four more hours. After concentrating the solution in vacuo, the residue was dissolved in methylene chloride and the solution was washed with saturated aqueous sodium bicarbonate followed by brine, then dried over magnesium sulfate and concentrated in vacuo. The solid residue was slurried in 50% ether in hexane for several minutes then filtered to yield 8.4 g of the title compound; m.p. 102°–104° C.

NMR (CDCl$_3$)δ: 8.9–7.0 (m, 3H, Ar); 5.1 (broad, 2H, NH$_2$); 3.2 (s, 2H, CH$_2$); and 1.6 (s, 6H, CH$_3$).

IR (nujol): 3300 cm$^{-1}$ (NH).

EXAMPLE 15

2,3-Dihydro-2,2-dimethyl-7-benzo[b]thiophenesulfonylisocyanate

To a refluxing solution of 8.6 g of 2,3-dihydro-2,2-dimethyl-7-benzo[b]thiophenesulfonamide (Example 14), 4.0 ml of n-butylisocyanate and 0.1 g of DABCO in 100 ml of xylenes was added 3.0 ml of phosgene at such a rate that the reaction temperature did not drop below 135° C. The mixture was refluxed for 1.5 hours, then the excess phosgene was purged with a stream of dry nitrogen. The mixture was cooled, filtered and concentrated in vacuo to yield the title compound as an oil. The crude yield was assumed to be near quantitative. IR (neat) 2220 cm$^{-1}$ (NCO).

The oil was diluted to a volume of 88 ml with dry acetonitrile for use as a stock solution in subsequent reactions.

EXAMPLE 16

N-[(4-Cyclopropyl-6-methoxy-1,3,5-triazin-2-yl)aminocarbonyl]-2,3-dihydro-2,2-dimethyl-7-benzothiophenesulfonamide To 22 ml of the sulfonylisocyanate stock solution prepared in the previous Example (15) is added 0.85 g of 2-amino-4-cyclopropyl-6-methoxy-1,3,5-triazine in one portion. The mixture is heated to reflux and stirred for 16 hours at room temperature for 24 hours. The suspension is concentrated in vacuo and the residue in triturated with ethyl acetate to give the subject compound.

EXAMPLE 17

7-Nitrobenzo[b]thiophene 1,1-dioxide

To a solution of 24.8 g of 7-nitrobenzo[b]thiophene in 200 ml of glacial acetic acid pre-heated to 100° C. was added 90 ml of a 30% aqueous solution of hydrogen peroxide at such a rate that the temperature remained between 100° to 105° C. The solution was refluxed for one hour, then 200 ml of water was added and the mixture was cooled in an ice-bath and filtered. The solid residue was washed sequentially with water, ethanol and ether to yield 20 g of the title compound; m.p. 195°–197° C.

NMR (CDCl$_3$+DMSO)δ: 8.5 (m, 1H, Ar); 8.0 (m, 2H, Ar); 7.6 (m, 1H, Ar); and 7.2 (m, 1H, Ar).

IR (nujol): 1540 and 1300 cm$^{-1}$.

EXAMPLE 18

7-Amino-2,3-dihydrobenzo[b]thiophene 1,1-dioxide

7-Nitrobenzo[b]thiophene-1,1-dioxide (19 g, Example 17) was hydrogenated in 200 ml of ethyl acetate over 1.0 g of 10% palladium-on-charcoal catalyst at 500 pounds-per-square-inch of pressure and 100° C. until no more hydrogen gas was absorbed. The mixture was filtered through celite, and the filtrate was concentrated in vacuo. The solid residue was recrystallized from 1-chlorobutane to yield 13.2 g of the title compound; m.p. 117°–119° C.

NMR (CDCl$_3$+DMSO)δ: 7.3–6.7 (m, 3H, Ar); 5.1 (broad, 2H, NH$_2$); and 3.4 (m, 4H, CH$_2$).

IR (nujol): 3400, 3300, 1630 and 1590 cm$^{-1}$.

EXAMPLE 19

2,3-Dihydro-7-benzo[b]thiophenesulfonamide 1,1-dioxide

A. A diazonium salt was prepared by adding a solution of 5.3 g of sodium nitrite in 10 ml of water to a suspension containing 12.8 g of 7-amino-2,3-dihydrobenzo[b]thiophene-1,1-dioxide (Example 18), 25 ml of glacial acetic acid and 75 ml of concentrated hydrochloric acid, cooled at −5° to 5° C. during the addition. After stirring for 0.5 hour at 0° C., the diazonium salt suspension was added dropwise to a mixture consisting of 75 ml of concentrated hydrochloric acid, 50 ml of glacial acetic acid, 1.0 g of cupric chloride dihydrate and 8.0 ml of liquified sulfur dioxide, cooled at −5° C. during the addition. The mixture was stirred at 0° C. for one hour and at 20° C. for two hours, then diluted with excess water and stirred to yield a precipitate. The mixture was filtered and the solid residue was washed with water to yield crude 2,3-dihydro-7-benzo[b]thiophenesulfonyl chloride-1,1-dioxide.

B. The above sulfonyl chloride was dissolved in methylene chloride and dried over magnesium sulfate. The dried solution was contacted with 5.0 ml of liquified ammonia at −7° C., then stirred at 20° C. for 18 hours. The suspension was concentrated in vacuo, and the residue was slurried in 100 ml of 10% hydrochloric acid, then filtered. The solid residue was washed with water and ether to yield 11.5 g of the title compound; m.p. 215°–217° C.

NMR (CDCl$_3$+DMSO)δ: 8.1–7.6 (m, 3H, Ar); 7.0 (broad, 2H, NH$_2$); and 3.8–3.3 (m, 4H, CH$_{2L}$).

IR (nujol): 3300, 3200 and 1350 cm$^{-1}$.

EXAMPLE 20

N-[(4-Cyclopropryl-6-methoxy-1,3,5-triazin-2-yl)aminocarbonyl]-2,3-dihydro-7-benzothiophene-1,1-dioxide A suspension of 1.0 g of the sulfonamide prepared in Example 19 in 100 ml of dry methylene chloride is added 2.5 ml of a 20% solution of trimethylaluminum in toluene under a blanket of dry nitrogen. After stirring at 20° C. for 0.25 hour, 1.14 g of methyl (4-cyclopropyl-6-methoxy-1,3,5-triazine)carbamate is added in one portion and the suspension is refluxed for 24 hours. The suspension is cooled in an ice-bath while 20 ml of 1N hydrochloric acid is slowly added. After several minutes of stirring, the organic layer is separated, washed with water, dried over magnesium sulfate and concentrated in vacuo. The residue is triturated with ethyl acetate to give the subject compound.

Using the techniques described in Equations 1–7 and Examples 5, 11, 16 and 20, or simple modifications thereof, the following compounds in Tables I–IV can be made by one skilled in the art.

TABLE I

| $R_1$ | $R_2$ | $R_3$ | $R_4$ | $R_5$ | $R_{12}$ | W | O | Y | Z | m.p. (°C.) |
|---|---|---|---|---|---|---|---|---|---|---|
| H | H | H | H | H | H | O | Q | $CH_3$ | CH | |
| H | H | H | H | H | H | O | O | $C_2H_5$ | CH | |
| H | H | H | H | H | H | O | O | $CH_2OCH_3$ | CH | |
| H | H | H | H | H | H | O | O | $CH_2OC_2H_5$ | CH | |
| H | H | H | H | H | H | O | O | $OCH_3$ | CH | |
| H | H | H | H | H | H | O | O | $OC_2H_5$ | CH | |
| H | H | H | H | H | H | O | O | $OCF_2H$ | CH | |
| H | H | H | H | H | H | O | O | $SCF_2H$ | CH | |
| H | H | H | H | H | H | O | O | $OCH_2CF_3$ | CH | |
| H | H | H | H | H | H | O | O | $OCH_2CH_2F$ | CH | |
| H | H | H | H | H | H | O | O | $OCH_2CH=CH_2$ | CH | |
| H | H | H | H | H | H | O | O | $OCH_2C\equiv CH$ | CH | |
| H | H | H | H | H | H | O | O | $NHCH_3$ | CH | |
| H | H | H | H | H | H | O | O | $N(CH_3)_2$ | CH | |
| H | H | H | H | H | H | O | O | $CH(OCH_3)_2$ | CH | |
| $CH_3$ | H | H | H | H | H | O | O | $CH_3$ | CH | |
| $CH_3$ | H | H | H | H | H | O | O | $C_2H_5$ | CH | |
| $CH_3$ | H | H | H | H | H | O | O | $CH_2OCH_3$ | CH | |
| H | $CH_3$ | H | H | H | H | O | O | $CH_2OC_2H_5$ | CH | |
| H | $CH_3$ | H | H | H | H | O | O | $OCH_3$ | CH | |
| H | $CH_3$ | H | H | H | H | O | O | $OC_2H_5$ | CH | |
| H | $CH_3$ | H | H | H | H | O | O | $OCF_2H$ | CH | |
| $CH_3$ | H | H | H | H | H | O | O | $SCF_2H$ | CH | |
| $CH_3$ | H | H | H | H | H | O | O | $OCH_2CF_3$ | CH | |
| $CH_3$ | H | H | H | H | H | O | O | $OCH_2CH_2F$ | CH | |
| $CH_3$ | H | H | H | H | H | O | O | $OCH_2CH=CH_2$ | CH | |
| $CH_3$ | H | H | H | H | H | O | O | $OCH_2C\equiv CH$ | CH | |
| $CH_3$ | H | H | H | H | H | O | O | $NHCH_3$ | CH | |
| $CH_3$ | H | H | H | H | H | O | O | $N(CH_3)_2$ | CH | |
| $CH_3$ | H | H | H | H | H | O | O | $CH(OCH_3)_2$ | CH | |
| $CH_3$ | $CH_3$ | H | H | H | H | O | O | $CH_3$ | CH | |
| $CH_3$ | $CH_3$ | H | H | H | H | O | O | $C_2H_5$ | CH | |
| $CH_3$ | $CH_3$ | H | H | H | H | O | O | $CH_2OCH_3$ | CH | |
| $CH_3$ | $CH_3$ | H | H | H | H | O | O | $OCH_3$ | CH | |
| $CH_3$ | $CH_3$ | H | H | H | H | O | O | $OC_2H_5$ | CH | |
| $CH_3$ | $CH_3$ | H | H | H | H | O | O | $OCF_2H$ | CH | |
| $CH_3$ | $CH_3$ | H | H | H | H | O | O | $OCH_2CF_3$ | CH | |
| $CH_3$ | $CH_3$ | H | H | H | H | O | O | $OCH_2CH_2F$ | CH | |
| $CH_3$ | $CH_3$ | H | H | H | H | O | O | $OCH_2CH=CH_2$ | CH | |
| $CH_3$ | $CH_3$ | H | H | H | H | O | O | $OCH_2C\equiv CH$ | CH | |
| $CH_3$ | $CH_3$ | H | H | H | H | O | O | $NHCH_3$ | CH | |
| $CH_3$ | $CH_3$ | H | H | H | H | O | O | $N(CH_3)_2$ | CH | |
| $CH_3$ | $CH_3$ | H | H | H | H | O | O | $CH(OCH_3)_2$ | CH | |
| $CH_3$ | H | $CH_3$ | H | H | H | O | O | $CH_3$ | CH | |
| H | $CH_3$ | $CH_3$ | H | H | H | O | O | $C_2H_5$ | CH | |
| H | $CH_3$ | $CH_3$ | H | H | H | O | O | $CH_2OCH_3$ | CH | |
| $CH_3$ | H | $CH_3$ | H | H | H | O | O | $OCH_3$ | CH | |
| $CH_3$ | H | $CH_3$ | H | H | H | O | O | $OC_2H_5$ | CH | |
| $CH_3$ | H | $CH_3$ | H | H | H | O | O | $OCF_2H$ | CH | |
| $CH_3$ | H | $CH_3$ | H | H | H | O | O | $OCH_2CF_3$ | CH | |
| $CH_3$ | H | $CH_3$ | H | H | H | O | O | $OCH_2CH_2F$ | CH | |
| $CH_3$ | H | $CH_3$ | H | H | H | O | O | $OCH_2CH=CH_2$ | CH | |
| $CH_3$ | H | $CH_3$ | H | H | H | O | O | $CH(OCH_3)_2$ | CH | |
| $C_2H_5$ | H | H | H | H | H | O | O | $CH_3$ | CH | |
| n-$C_3H_7$ | H | H | H | H | H | H | O | $CH_3$ | CH | |
| $CH(CH_3)_2$ | H | H | H | H | H | O | O | $CH_3$ | CH | |
| H | H | H | Cl | CH | H | O | O | $CH_3$ | CH | |
| H | H | H | Cl | H | H | O | O | $OCH_3$ | CH | |
| $CH_3$ | H | H | Cl | H | H | O | O | $OCH_3$ | CH | |
| H | H | H | Cl | H | H | O | O | $OC_2H_5$ | CH | |
| H | $CH_3$ | H | Cl | H | H | O | O | $OCF_2H$ | CH | |
| H | H | H | Cl | H | H | O | O | $OCH_2CF_3$ | CH | |

TABLE I-continued

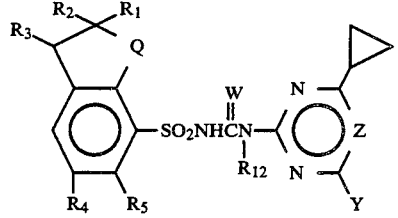

| $R_1$ | $R_2$ | $R_3$ | $R_4$ | $R_5$ | $R_{12}$ | W | O | Y | Z | m.p. (°C.) |
|---|---|---|---|---|---|---|---|---|---|---|
| H | CH$_3$ | H | Cl | H | H | O | O | OCH$_2$CH$_2$F | CH | |
| H | H | H | Cl | H | H | O | O | CH(OCH$_3$)$_2$ | CH | |
| CH$_3$ | H | H | Br | H | H | O | O | CH$_3$ | CH | |
| H | CH$_3$ | H | Br | H | H | O | O | C$_2$H$_5$ | CH | |
| CH$_3$ | H | H | Br | H | H | O | O | OCH$_3$ | CH | |
| H | H | H | Br | H | H | O | O | OCH$_3$ | CH | |
| H | H | H | Br | H | H | O | O | OCF$_2$H | CH | |
| CH$_3$ | H | H | Br | H | H | O | O | OCH$_2$CF$_3$ | CH | |
| CH$_3$ | H | H | Br | H | H | O | O | OCH$_2$CH$_2$F | CH | |
| CH$_3$ | H | H | Br | H | H | O | O | CH(OCH$_3$)$_2$ | CH | |
| CH$_3$ | H | H | CH$_3$ | H | H | O | O | CH$_3$ | CH | |
| CH$_3$ | H | H | CH$_3$ | H | H | O | O | OCH$_3$ | CH | |
| CH$_3$ | H | H | OCH$_3$ | H | H | O | CH$_3$ | CH | | |
| CH$_3$ | H | H | OCH$_3$ | H | H | O | OCH$_3$ | CH | | |
| H | CH$_3$ | H | CF$_3$ | H | H | O | O | OCH$_3$ | CH | |
| H | CH$_3$ | H | CF$_3$ | H | H | O | O | CH$_3$ | CH | |
| H | H | H | H | H | H | O | SO$_2$ | CH$_3$ | CH | |
| H | H | H | H | H | H | O | SO$_2$ | C$_2$H$_5$ | CH | |
| H | H | H | H | H | H | O | SO$_2$ | OCH$_3$ | CH | |
| H | H | H | H | H | H | O | SO$_2$ | OC$_2$H$_5$ | CH | |
| H | H | H | H | H | H | O | SO$_2$ | OCF$_2$H | CH | |
| H | H | H | H | H | H | O | SO$_2$ | OCH$_2$CF$_3$ | CH | |
| H | H | H | H | H | H | O | SO$_2$ | OCH$_2$CH$_2$F | CH | |
| CH$_3$ | H | H | H | H | H | O | SO$_2$ | CH$_3$ | CH | |
| CH$_3$ | H | H | H | H | H | O | SO$_2$ | C$_2$H$_5$ | CH | |
| CH$_3$ | H | H | H | H | H | O | SO$_2$ | CH$_2$OCH$_3$ | CH | |
| CH$_3$ | H | H | H | H | H | O | SO$_2$ | CH$_2$OC$_2$H$_5$ | CH | |
| CH$_3$ | H | H | H | H | H | O | SO$_2$ | OCH$_3$ | CH | |
| CH$_3$ | H | H | H | H | H | O | SO$_2$ | OC$_2$H$_5$ | CH | |
| CH$_3$ | H | H | H | H | H | O | SO$_2$ | OCF$_2$H | CH | |
| H | CH$_3$ | H | H | H | H | O | SO$_2$ | SCF$_2$H | CH | |
| H | CH$_3$ | H | H | H | H | O | SO$_2$ | OCH$_2$CF$_3$ | CH | |
| H | CH$_3$ | H | H | H | H | O | SO$_2$ | OCH$_2$CH$_2$F | CH | |
| H | CH$_3$ | H | H | H | H | O | SO$_2$ | OCH$_2$CH=CH$_2$ | CH | |
| H | CH$_3$ | H | H | H | H | O | SO$_2$ | OCH$_2$C≡CH | CH | |
| H | CH$_3$ | H | H | H | H | O | SO$_2$ | NHCH$_3$ | CH | |
| H | CH$_3$ | H | H | H | H | O | SO$_2$ | N(CH$_3$)$_2$ | CH | |
| H | CH$_3$ | H | H | H | H | O | SO$_2$ | CH(OCH$_3$)$_2$ | CH | |
| CH$_3$ | CH$_3$ | H | H | H | H | O | SO$_2$ | CH$_3$ | CH | |
| CH$_3$ | CH$_3$ | H | H | H | H | O | SO$_2$ | OCH$_3$ | CH | |
| CH$_3$ | CH$_3$ | H | H | H | H | O | SO$_2$ | OC$_2$H$_5$ | CH | |
| CH$_3$ | CH$_3$ | H | H | H | H | O | SO$_2$ | OCF$_2$H | CH | |
| CH$_3$ | CH$_3$ | H | H | H | H | O | SO$_2$ | C$_2$H$_5$ | CH | |
| C$_2$H$_5$ | H | H | H | H | H | O | SO$_2$ | CH$_3$ | CH | |
| n-C$_3$H$_7$ | H | H | H | H | H | O | SO$_2$ | CH$_3$ | CH | |
| H | H | CH$_3$ | H | H | H | O | SO$_2$ | CH$_3$ | CH | |
| H | H | H | H | H | H | O | S | CH$_3$ | CH | |
| CH$_3$ | H | H | H | H | H | O | S | OCH$_3$ | CH | |
| CH$_3$ | H | H | H | H | H | O | S | CH$_3$ | CH | |
| CH$_3$ | CH$_3$ | H | H | H | H | O | S | OCH$_3$ | CH | |
| CH$_3$ | CH$_3$ | H | H | H | H | O | S | CH$_3$ | CH | |
| C$_2$H$_5$ | H | H | H | H | H | O | S | CH$_3$ | CH | |
| n-C$_3$H$_7$ | H | H | H | H | H | O | S | CH$_3$ | CH | |
| CH$_3$ | H | CH$_3$ | H | H | H | O | S | CH$_3$ | CH | |
| CH$_3$ | H | H | CH$_3$ | H | H | O | SO$_2$ | CH$_3$ | CH | |
| CH$_3$ | H | H | H | H | CH$_3$ | O | O | CH$_3$ | CH | |
| CH$_3$ | H | H | H | H | CH$_3$ | O | SO$_2$ | CH$_3$ | CH | |
| CH$_3$ | H | H | H | H | H | S | O | CH$_3$ | CH | |
| CH$_3$ | H | H | H | H | H | S | SO$_2$ | CH$_3$ | CH | |
| CH$_3$ | H | H | H | CH$_3$ | H | O | SO$_2$ | CH$_3$ | CH | |
| CH$_3$ | H | H | H | OCH$_3$ | H | O | O | OCH$_3$ | CH | |
| CH$_3$ | CH$_3$ | H | H | Cl | H | O | S | OCH$_3$ | CH | |
| CH$_3$ | H | H | H | Br | H | O | O | OCH$_3$ | N | |
| CH$_3$ | H | H | H | NO$_2$ | H | O | O | CH$_3$ | CH | |
| CH$_3$ | H | H | H | CO$_2$CH$_3$ | H | O | O | OC$_2$H$_5$ | N | |
| CH$_3$ | H | H | H | CO$_2$C$_2$H$_5$ | H | O | SO$_2$ | CH$_3$ | CH | |
| CH$_3$ | H | H | H | CO$_2$CH$_2$CH$_2$CH$_3$ | H | O | O | CH$_3$ | CH | |
| CH$_3$ | CH$_3$ | H | H | CO$_2$CH(CH$_3$)$_2$ | H | O | S | OCH$_3$ | CH | |
| CH$_3$ | H | H | H | CO$_2$CH$_2$CH=CH$_2$ | H | O | O | CH$_3$ | CH | |

TABLE I-continued

| R₁ | R₂ | R₃ | R₄ | R₅ | R₁₂ | W | O | Y | Z | m.p. (°C.) |
|---|---|---|---|---|---|---|---|---|---|---|
| CH₃ | H | H | H | CO₂CH₂CH₂OCH₃ | H | O | O | CH₃ | CH | |
| CH₃ | H | H | H | CO₂CH₂CH₂Cl | H | O | O | OCH₃ | CH | |
| CH₃ | CH₃ | H | H | SO₂C₂H₅ | H | O | O | CH₃ | CH | |
| CH₃ | H | H | H | SO₂CH₂CH₂CH₃ | H | O | O | OCH₃ | CH | |
| CH₃ | H | H | H | SO₂CH₂(CH₃)₂ | H | O | O | CH₃ | CH | |
| H | CH₃ | H | H | OSO₂CH₃ | H | O | SO₂ | CH₃ | CH | |
| CH₃ | H | H | H | OSO₂C₂H₅ | H | O | O | CH₃ | CH | |
| CH₃ | H | H | H | OSO₂CH₂CH₂CH₃ | H | O | O | CH₃ | CH | |
| CH₃ | H | H | H | OSO₂CH(CH₃)₂ | H | O | S | CH₃ | CH | |
| CH₃ | CH₃ | H | H | OSO₂CF₃ | H | O | O | OCH₃ | N | |
| CH₃ | H | H | H | SO₂N(CH₃)₂ | H | O | O | CH₃ | CH | |
| CH₃ | H | H | H | SO₂N(CH₃)C₂H₅ | H | O | O | CH₃ | CH | |
| H | H | H | H | H | H | O | O | CH₃ | N | |
| H | H | H | H | H | H | O | O | OCH₃ | N | 182–187 |
| H | H | H | H | H | H | O | O | OC₂H₅ | N | |
| H | H | H | H | H | H | O | O | SCF₂H | N | |
| H | H | H | H | H | H | O | O | OCH₂CF₃ | N | |
| H | H | H | H | H | H | O | O | OCH₂CH₂F | N | |
| H | H | H | H | H | H | O | O | OCH₂CH═CH₂ | N | |
| H | H | H | H | H | H | O | O | OCH₂C≡CH | N | |
| CH₃ | H | H | H | SO₂N(OCH₃)CH₃ | H | O | O | OCH₃ | CH | |
| H | H | H | H | H | H | O | O | NHCH₃ | N | |
| H | H | H | H | H | H | O | O | NH(CH₃)₂ | N | |
| H | H | H | H | H | H | O | O | CH(OCH₃)₂ | N | |
| CH₃ | H | H | H | H | H | O | O | OCH₃ | N | |
| CH₃ | H | H | H | H | H | O | O | OCH₂H₅ | N | |
| H | CH₃ | H | H | H | H | O | O | OCH₂CF₃ | N | |
| H | CH₃ | H | H | H | H | O | O | OCH₂CH₂F | N | |
| H | CH₃ | H | H | H | H | O | O | OCH₂CH═CH₂ | N | |
| CH₃ | CH₃ | H | H | H | H | O | O | OCH₃ | N | |
| CH₃ | CH₃ | H | H | H | H | O | O | OC₂H₅ | N | |
| CH₃ | H | CH₃ | H | H | H | O | O | OCH₃ | N | |
| H | CH₃ | CH₃ | H | H | H | O | O | OC₂H₅ | N | |
| C₂H₅ | H | H | H | H | H | O | SO₂ | OCH₃ | N | |
| CH(CH₃)₂ | H | H | H | H | H | H | O | OCH₃ | N | |
| n-propyl | | | H | H | H | H | O | OCH₃ | N | |
| CH₃ | H | H | Cl | H | H | O | O | OCH₃ | N | |
| H | H | H | Cl | H | H | O | O | OC₂H₅ | N | |
| CH₃ | H | H | Br | H | H | O | O | OCH₃ | N | |
| H | H | H | Cl | H | H | O | O | OCH₃ | N | |
| CH₃ | H | H | CH₃ | H | H | O | O | OCH₃ | N | |
| CH₃ | H | H | OCH₃ | H | H | O | O | OCH₃ | N | |
| CH₃ | H | H | CF₃ | H | H | O | O | OCH₃ | N | |
| H | H | H | H | H | H | O | SO₂ | OCH₃ | N | 234–236(d) |
| H | H | H | H | H | H | O | SO₂ | OC₂H₅ | N | |
| CH₃ | H | H | H | H | H | O | SO₂ | CH₃ | N | |
| CH₃ | H | H | H | H | H | O | SO₂ | OCH₃ | N | 205–210(d) |
| CH₃ | H | H | H | H | H | O | SO₂ | OC₂H₅ | N | |
| CH₃ | H | H | H | H | H | O | SO₂ | C₂H₅ | N | |
| CH₃ | H | H | H | H | H | O | SO₂ | SCF₂H | N | |
| H | CH₃ | H | H | H | H | O | SO₂ | OCH₂CF₃ | N | |
| H | CH₃ | H | H | H | H | O | SO₂ | OCH₂CH₂F | N | |
| H | CH₃ | H | H | H | H | O | SO₂ | OCH₂CH═CH₂ | N | |
| H | CH₃ | H | H | H | H | O | SO₂ | OCH₂C≡CH | N | |
| H | CH₃ | H | H | H | H | O | SO₂ | NHCH₃ | N | |
| H | CH₃ | H | H | H | H | O | SO₂ | N(CH₃)₂ | N | |
| CH₃ | CH₃ | H | H | H | H | O | SO₂ | OCH₃ | N | |
| C₂H₅ | H | H | H | H | H | O | SO₂ | OCH₃ | N | |
| n-C₃H₇ | H | H | H | H | H | O | SO₂ | OCH₃ | N | |
| H | H | CH₃ | H | H | H | O | SO₂ | OCH₃ | N | |
| H | H | H | H | H | H | O | S | OCH | N | |
| CH₃ | H | H | H | H | H | O | S | OCH₃ | N | |
| CH₃ | CH₃ | H | H | H | H | O | S | OCH₃ | N | |
| C₂H₅ | H | H | H | H | H | O | S | OCH₃ | N | |
| n-C₃H₇ | H | H | H | H | H | O | S | OCH₃ | N | |
| CH₃ | H | H | CH₃ | H | H | O | SO₂ | OCH₃ | N | |
| CH₃ | H | H | H | H | CH₃ | O | SO₂ | OCH₃ | N | |
| CH₃ | H | H | H | Cl | H | O | SO₂ | OCH₃ | N | |
| CH₃ | H | H | H | CH₃ | H | O | SO₂ | OCH₃ | N | |

TABLE I-continued

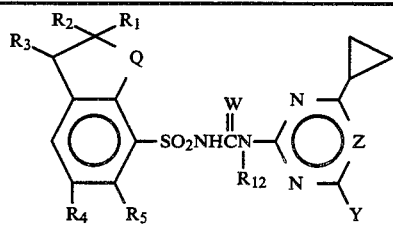

| R₁ | R₂ | R₃ | R₄ | R₅ | R₁₂ | W | O | Y | Z | m.p. (°C.) |
|---|---|---|---|---|---|---|---|---|---|---|
| CH₃ | H | H | H | H | H | S | O | OCH₃ | N | |
| CH₃ | H | H | H | Cl | H | O | SO₂ | OC₂H₅ | N | |
| CH₃ | H | H | H | CH₃ | H | O | SO₂ | OC₂H₅ | N | |
| CH₃ | H | H | H | H | H | O | SO | OCH₃ | CH | |
| n-butyl | H | H | H | H | H | O | SO₂ | OCH₃ | N | |
| H | C₂H₅ | H | H | H | H | O | O | OCH₃ | N | |
| H | n-propyl | H | H | H | H | O | SO₂ | OCH₃ | N | |
| H | CH(CH₃)₂ | H | H | H | H | O | SO₂ | OCH₃ | N | |
| H | n-butyl | H | H | H | H | O | O | OCH₃ | N | |
| CH₃ | H | H | F | H | H | O | O | OCH₃ | N | |
| CH₃ | H | H | SCH₃ | H | H | O | O | OCH₃ | N | |
| CH₃ | H | H | OCF₂H | H | H | O | O | OCH₃ | N | |
| CH₃ | H | H | H | F | H | O | O | OCH₃ | N | |
| CH₃ | H | H | H | CF₃ | H | O | O | OCH₃ | N | |
| CH₃ | H | H | H | SCH₃ | H | O | O | OCH₃ | N | |
| CH₃ | H | H | H | OCF₂H | H | O | O | OCH₃ | N | |
| CH₃ | H | H | H | H | H | O | O | CF₃ | N | |
| H | H | H | Br | H | H | O | O | OCH₃ | N | |
| CH₃ | H | H | H | Cl | H | O | SO₂ | OCH₃ | N | |

TABLE II

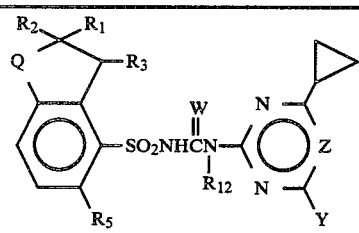

| R₁ | R₂ | R₃ | R₅ | R₁₂ | W | Q | Y | Z | m.p. °C. |
|---|---|---|---|---|---|---|---|---|---|
| H | H | H | H | H | O | O | OCH₃ | CH | |
| H | H | H | H | H | O | O | OCH₃ | N | |
| CH₃ | H | CH₃ | H | H | O | SO₂ | OCH₃ | CH | |
| H | H | H | H | H | O | S | OCH₃ | CH | |
| H | H | H | H | H | S | O | OCH₃ | CH | |
| H | CH₃ | CH₃ | H | H | O | SO₂ | OCH₃ | N | |
| H | H | H | H | CH₃ | O | O | OCH₃ | CH | |

TABLE III

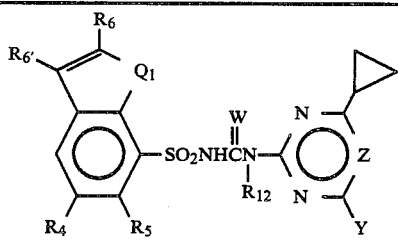

| R₄ | R₅ | R₆ | R₆' | R₁₂ | W | Q₁ | Y | Z | m.p. °C. |
|---|---|---|---|---|---|---|---|---|---|
| H | H | H | H | H | O | O | OCH₃ | CH | |
| H | H | H | H | H | O | O | OCH₃ | N | |
| H | H | CH₃ | H | H | O | O | OCH₃ | CH | |
| H | H | CH₃ | H | H | O | S | OCH₃ | CH | |
| H | H | CH₃ | H | H | O | O | OC₂H₅ | N | |
| H | H | CH₃ | CH₃ | H | O | SO₂ | OCH₃ | CH | |
| H | H | C₂H₅ | H | H | O | O | OCH₃ | CH | |

TABLE III-continued

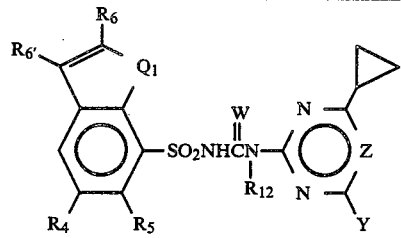

| R₄ | R₅ | R₆ | R₆' | R₁₂ | W | Q₁ | Y | Z | m.p. °C. |
|---|---|---|---|---|---|---|---|---|---|
| H | H | n-C₃H₇ | H | H | O | O | OC₂H₅ | N | |
| H | H | Cl | CH₃ | H | O | O | OCH₃ | CH | |
| H | H | Br | CH₃ | H | O | O | OCH₃ | CH | |
| H | H | CH₃ | Cl | H | O | O | OCH₃ | N | |
| H | H | CH₃ | Br | H | O | O | OCH₃ | CH | |
| H | H | CH₃ | CH₃ | H | O | S | OCH₃ | CH | |
| Cl | H | CH₃ | H | H | O | O | OCH₃ | CH | |
| CH₃ | H | CH₃ | H | H | O | O | OCH₃ | CH | |
| H | Cl | CH₃ | H | H | O | O | OCH₃ | CH | |
| H | H | n-butyl | H | H | O | O | OCH₃ | CH | |

TABLE IV

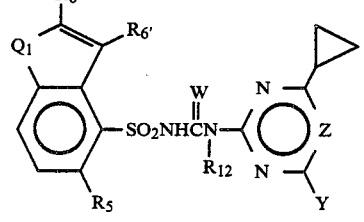

| R₅ | R₆ | R₆' | R₁₂ | W | Q₁ | Y | Z | m.p. °C. |
|---|---|---|---|---|---|---|---|---|
| H | H | CH₃ | H | O | O | OCH₃ | CH | |
| H | CH₃ | CH₃ | H | O | O | OCH₃ | CH | |
| H | H | H | H | O | S | OCH₃ | CH | |

TABLE IV-continued

[Chemical structure showing a benzene ring with substituents $Q_1$, $R_6$, $R_{6'}$, $R_5$, connected via $SO_2NHC(=W)N(R_{12})$ to a pyrimidine/triazine ring with substituents including cyclopropyl, Y, Z]

| $R_5$ | $R_6$ | $R_{6'}$ | $R_{12}$ | W | $Q_1$ | Y | Z | m.p. °C. |
|---|---|---|---|---|---|---|---|---|
| H | H | CH$_3$ | H | O | SO$_2$ | OCH$_3$ | CH | |
| H | H | CH$_3$ | H | O | O | OCH$_3$ | N | |
| H | H | CH$_3$ | H | O | SO$_2$ | OCH$_3$ | N | |

Formulations

Useful formulations of the compounds of Formulae I, I', II and II' can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE V

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples all parts are by weight unless otherwise indicated.

EXAMPLE 21

Wettable Powder

N-[4-cyclopropyl-6-methylpyrimidin-2-yl)aminocarbonyl]-2,3-dihydro-2-methyl-7-benzothiophenesulfonamide, 1,1-dioxide—80%
sodium alkylnaphthalenesulfonate—2%
sodium ligninsulfonate—2%
synthetic amorphous silica—3%
kaolinite—13%

The ingredients are blended, hammer-milled until all the solids are essentially under 50 microns, reblended, and packaged.

EXAMPLE 22

Oil Suspension

N-[(4-cyclopropyl-6-methylpyrimidin-2-yl)aminocarbonyl]2,3-dihydro-2-3-dimethyl-7-benzofuransulfonamide—25%
polyoxyethylene sorbitol hexaoleate—5%
highly aliphatic hydrocarbon oil—70%

The ingredients are ground together in a sand mill until the solid particles have been reduced to under about 5 microns. The resulting thick suspension may be applied directly, but preferably after being extended with oils or emulsified in water.

EXAMPLE 23

Wettable Powder

N-[(4-cyclopropyl-6-methylpyrimidin-2-yl)aminocarbonyl]-B 2,3-dihydro-2-methyl-7-benzothiophenesulfonamide,1,1-dioxide—20%
sodium alkylnaphthalenesulfonate—4%
sodium ligninsulfonate—4%
low viscosity methyl cellulose—3%
attapulgite—69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 24

Low Strength Granule

N-[(4-cyclopropyl-6-methoxy-1,3,5-triazin-2-yl)aminocarbonyl]-2,3-dihydro-7-benzothiophenesulfonamide—0.1%
attapulgite granules (U.S.S. 20–40 mesh)—99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 25

Granule

N-[(4-cyclopropyl-6-methoxy-1,3,5-triazin-2-yl)aminocarbonyl]-2,3-dihydro-2-2-dimethyl-7-benzothiophenesulfonamide—80%
wetting agent—1%
crude ligninsulfonate salt (containing 5-20% of the natural sugars)—10%
attapulgite clay—9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 4–100 mesh (1410–149 microns), and packaged for use.

EXAMPLE 26

High Strength Concentrate

N-[(4-cyclopropyl-6-methoxy-1,3,5-triazin-2-yl)aminocarbonyl]-2,3-dihydro-7-benzothiophenesulfonamide-1,1-dioxide—99%
silica aerogel—0.5%
synthetic amorphous silica—0.5%

The ingredients are blended and ground in a hammer-mill to produce a material essentially all passing a U.S.S. No. 50 screen (0.3 mm opening). The concentrate may be formulated further if necessary.

Utility

The compounds of the present invention are effective herbicides. They have utility for broadspectrum pre- and/or post-emergence weed control in areas where complete control of all vegetation is desired, such as around fuel storage tanks, ammunition depots, industrial storage areas, parking lots, drive-in theaters, around billboards, highway and railroad structures, or on fallow land.

The rates of application for the compounds of the invention are determined by a number of factors, including the types of weeds to be controlled, weather and climate, formulations selected, mode of application, amount of foliage present, etc. In general terms, the subject compounds should be applied at levels of around 0.005 to 5 kg/ha, the lower rates being suggested for use on lighter soils and/or those having a low organic matter content, or for situations where only short-term persistence is required.

The compounds of the invention may be used in combination with any other commercial herbicide examples of which are those of the triazine, triazole, uracil, urea, amide, diphenylether, carbamate, acetanilide, bipyridylium, dinitroaniline and phenolic types.

The herbicidal properties of the subject compounds were observed in greenhouse tests. The test procedures follow.

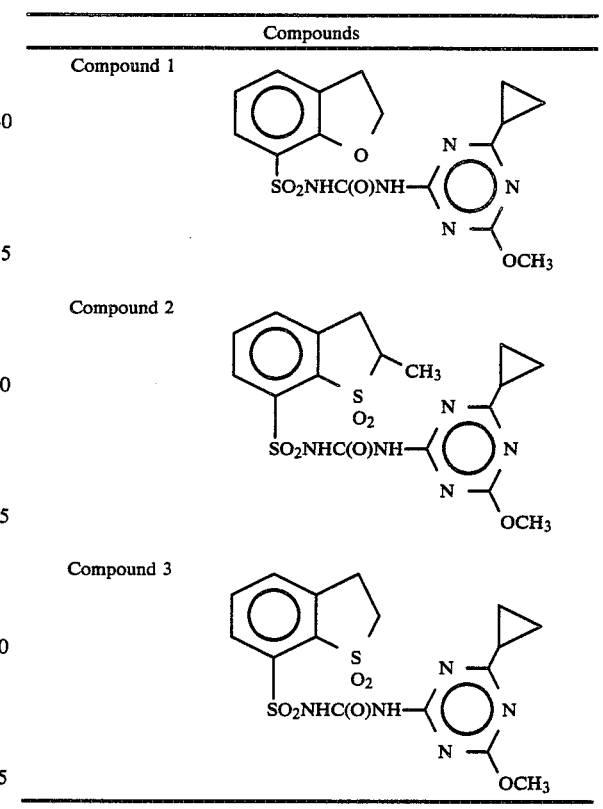

Test A

Seeds of crabgrass (Digitaria sp.), barnyardgrass (Echinochloa crusgalli), wild oats (Avena fatua), cheatgrass (Bromus secalinus), velvetleaf (Abutilon theophrasti), morningglory (Ipomoea sp.), clockbur (Xanthium pensylvanicum), sorghum, corn, soybean, sugar beet, rice, wheat and purple nutsedge (Cyperus rotundus) tubers were planted and treated pre-emergence with the chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings are based on a numerical scale extending from 0=no injury, to 10=complete kill. The accompanying descriptive symbols have the following meanings:
A=growth acceleration;
C=chlorosis/necrosis;
D=defoliation;
E=emergence inhibition;
G=growth retardation;
H=formative effects;
U=unusual pigmentation;
X=axillary stimulation; and
6Y=abscised buds or flowers.

TABLE A

| Rate kg/ha | Cmpd. 1 0.05 | Cmpd. 2 0.05 | Cmpd. 3 0.05 |
|---|---|---|---|
| POST-EMERGENCE | | | |
| Morningglory | 10C | 10C | 5C,9G |
| Cocklebur | 9C | 10C | 5C,9H |
| Velvetleaf | 9C | 9C | 4C,8G |
| Nutsedge | 3C,5G | 5C,9G | 3G |
| Crabgrass | 0 | 0 | 0 |
| Barnyardgrass | 3H | 0 | 0 |
| Cheatgrass | 5G | 0 | 0 |
| Wild Oats | 0 | 4C,9H | 3G |
| Wheat | 0 | 0 | 0 |
| Corn | 3C,9H | 9C | 4C,9G |
| Soybean | 3C,8H | 5C,9G | 3H,9G |
| Rice | 4C,9G | 9C | 8G |
| Sorghum | 3C,9H | 9C | 4C,9G |
| Sugar beet | 3C,9H | 10C | 5C,9H |
| Cotton | 3C,9H | 5C,9H | 9H |
| PRE-EMERGENCE | | | |
| Morningglory | 3C,8H | 9G | 8H |
| Cocklebur | 3C,5H | 9H | 0 |
| Velvetleaf | 8G | 3C,6H | 0 |
| Nutsedge | 0 | 5G | 0 |
| Crabgrass | 0 | 0 | 0 |
| Barnyardgrass | 0 | 2H | 0 |
| Cheatgrass | 5G | 5G | 4G |
| Wild Oats | 0 | 5C,9H | 3C,7G |
| Wheat | 0 | 0 | 0 |
| Corn | 3C,7H | 5C,9G | 3C,8H |
| Soybean | 3C,3H | 3C,6G | 2C,4H |
| Rice | 3C,9H | 10E | 3C,7G |

TABLE A-continued

| Rate kg/ha | Cmpd. 1 0.05 | Cmpd. 2 0.05 | Cmpd. 3 0.05 |
|---|---|---|---|
| Sorghum | 3C,8H | 5C,9H | 4C,9G |
| Sugar beet | 4C,9G | 9C | 4C,9G |
| Cotton | 7G | 6G | 3G |

Test B

Postemergence

Two round pans (25 cm diameter by 12.5 cm deep) were filled with Sassafras sandy loam soil. One pan was planted with blackgrass (*Alopecurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf, (*Abutilon theophrasti*), giant foxtail (*Setaria faberii*) and rape (*Brassica napus*). The other pan was planted with wheat, cotton, rice, corn, soybean, wild oats (*Avena fatua*), cocklebur (*Xantium pensylvanicum*), morningglory, (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Preemergence

Two round pans (25 cm diameter by 12.5 cm deep) were filled with Sassafras sandy loam soil. One pan was planted with blackgrass, sugar beets, nutsedge, crabgrass, sicklepod, teaweed, jimsonweed, velvetleaf, giant foxtail and rape. The other pan was planted with wheat, cotton, rice, corn, soybeans, wild oats, cocklebur, morningglory, johnsongrass, and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for plant response utilizing the rating system as described for Test A.

The response is rated on a scale of 0-100 with 0=no injury and 100=complete control.

Response ratings are contained in Table B.

TABLE B

| | SASSAFRAS SANDY LOAM | | | | | | | | | | |
|---|---|---|---|---|---|---|---|---|---|---|---|
| | Compound 1 | | | | Compound 2 | | | | Compound 3 | | |
| Rate g/ha | 250 | 62 | 16 | 4 | 250 | 62 | 16 | 4 | 62 | 16 | 4 |
| POST-EMERGENCE | | | | | | | | | | | |
| Corn | 100 | 100 | 30 | 0 | 100 | 100 | 100 | 90 | 100 | 90 | 20 |
| Wheat | 0 | 0 | 0 | 0 | 0 | 0 | 0 | 0 | 0 | 0 | 0 |
| Rice | 100 | 100 | 60 | 20 | 100 | 100 | 90 | 30 | 50 | 0 | 0 |
| Soybean | 100 | 70 | 20 | 0 | 100 | 100 | 90 | 50 | 100 | 70 | 20 |
| Cotton | 100 | 80 | 30 | 0 | 80 | 40 | 0 | 0 | 80 | 20 | 0 |
| Sugar beet | 100 | 100 | 90 | 70 | 100 | 100 | 100 | 90 | 100 | 100 | 50 |
| Rape | 100 | 100 | 90 | 50 | 100 | 100 | 100 | 50 | 100 | 90 | 40 |
| Crabgrass | 20 | 0 | 0 | 0 | 0 | 0 | 0 | 0 | 0 | 0 | 0 |
| Johnsongrass | 80 | 40 | 0 | 0 | 100 | 100 | 60 | 30 | 90 | 90 | 40 |
| Blackgrass | 100 | 70 | 30 | 0 | 100 | 100 | 100 | 40 | 50 | 20 | 0 |
| Barnyardgrass | 0 | 0 | 0 | 0 | 100 | 100 | 100 | 70 | 0 | 0 | 0 |
| Nutsedge | 40 | 0 | 0 | 0 | 100 | 100 | 40 | 0 | 0 | 0 | 0 |
| Giant Foxtail | 0 | 0 | 0 | 0 | 0 | 0 | 0 | 0 | 0 | 0 | 0 |
| Wild Oats | 20 | 0 | 0 | 0 | 100 | 70 | 30 | 0 | 0 | 0 | 0 |
| Cocklebur | 100 | 60 | 20 | 0 | 100 | 100 | 90 | 30 | 70 | 20 | 0 |
| Morningglory | 100 | 70 | 20 | 0 | 100 | 100 | 90 | 50 | 80 | 40 | 0 |
| Teaweed | 100 | 50 | 0 | 0 | 90 | 80 | 20 | 0 | 0 | 0 | 0 |
| Sicklepod | 40 | 0 | 0 | 0 | 100 | 90 | 40 | 0 | 40 | 0 | 0 |
| Jimsonweed | 90 | 70 | 30 | 0 | 100 | 100 | 70 | 0 | 70 | 50 | 20 |
| Velvetleaf | 100 | 100 | 20 | 0 | 100 | 100 | 70 | 30 | 70 | 30 | 0 |

TABLE B-continued

| | SASSAFRAS SANDY LOAM | | | | | | | | | | |
|---|---|---|---|---|---|---|---|---|---|---|---|
| | Compound 1 | | | | Compound 2 | | | | Compound 3 | | |
| Rate g/ha | 250 | 62 | 16 | 4 | 250 | 62 | 16 | 4 | 62 | 16 | 4 |
| | | | | | PRE-EMERGENCE | | | | | | |
| Corn | 100 | 40 | | | 100 | 90 | 30 | | 0 | 0 | |
| Wheat | 20 | 0 | | | 0 | 0 | 0 | | 0 | 0 | |
| Rice | 100 | 60 | | | 100 | 100 | 90 | | 70 | 0 | |
| Soybean | 80 | 20 | | | 70 | 30 | 0 | | 0 | 0 | |
| Cotton | 60 | 0 | | | 0 | 0 | 0 | | 0 | 0 | |
| Sugar beet | 100 | 60 | | | 100 | 100 | 80 | | 0 | 0 | |
| Rape | 80 | 20 | | | 100 | 90 | 30 | | 0 | 0 | |
| Crabgrass | 40 | 0 | | | 90 | 40 | 0 | | 20 | 0 | |
| Johnsongrass | 50 | 40 | | | 100 | 100 | 100 | | 80 | 0 | |
| Blackgrass | 80 | 30 | | | 100 | 100 | 80 | | 90 | 30 | |
| Barnyardgrass | 0 | 0 | | | 100 | 40 | 0 | | 0 | 0 | |
| Nutsedge | 0 | 0 | | | 100 | 100 | 40 | | 0 | 0 | |
| Giant Foxtail | 30 | 0 | | | 0 | 0 | 0 | | 0 | 0 | |
| Wild Oats | 0 | 0 | | | 90 | 70 | 20 | | 30 | 0 | |
| Cocklebur | 50 | 0 | | | 70 | 30 | 0 | | 20 | 0 | |
| Morningglory | 50 | 0 | | | 100 | 50 | 30 | | 20 | 0 | |
| Teaweed | 60 | 20 | | | 100 | 20 | 0 | | 0 | 0 | |
| Sicklepod | 50 | 20 | | | 80 | 30 | 0 | | 0 | 0 | |
| Jimsonweed | 80 | 20 | | | 100 | 90 | 20 | | 30 | 0 | |
| Velvetleaf | 90 | 40 | | | 90 | 60 | 0 | | 0 | 0 | |

What is claimed is:

1. A compound selected from:

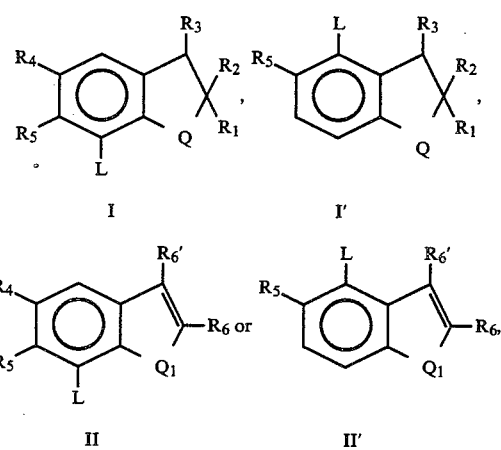

wherein

Q is O, S, SO or $SO_2$;
$Q_1$ is O, S or $SO_2$;
L is

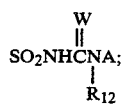

$R_1$ is H or $C_1$-$C_4$ alkyl;
$R_2$ is H or $C_1$-$C_4$ alkyl;
$R_3$ is H or $CH_3$;
$R_4$ is H, Cl, $CH_3$, $CF_3$, $OCH_3$, Br, F, $SCH_3$ or $OCF_2H$;
$R_5$ is H, $CH_3$, $OCH_3$, Cl, Br, $NO_2$, $CO_2R_7$, $SO_2R_8$, $OSO_2R_9$, $SO_2NR_{10}R_{11}$, F, $CF_3$, $SCH_3$, $OCF_2H$ or $SO_2N(OCH_3)CH_3$;
$R_6$ is H, Cl, Br or $C_1$-$C_4$ alkyl;
$R_6'$ is H, $CH_3$, Cl or Br;
$R_7$ is $C_1$-$C_3$ alkyl, $CH_2CH=CH_2$, $CH_2CH_2OCH_3$ or $CH_2CH_2Cl$;
$R_8$ is $C_1$-$C_3$ alkyl;
$R_9$ is $C_1$-$C_3$ alkyl or $CF_3$;
$R_{10}$ and $R_{11}$ are independently $C_1$-$C_2$ alkyl;
$R_{12}$ is H or $CH_3$;
W is O or S;
A is Y is $C_1$-$C_2$ alkyl, $C_1$-$C_2$ alkoxy, $C_1$-$C_2$ alkoxymethyl, $SCF_2H$, $OCH_2CF_3$, $OCH_2CH_2F$, $CF_3$, $OCH_2CH=CH_2$, $OCH_2C\equiv CH$, $NHCH_3$, $N(CH_3)_2$ or $CH(OCH_3)_2$; and
Z is N, and their agriculturally suitable salts; provided that
(1) in Formulae II and II', when $R_5$ is $NO_2$, then $R_6$ is $C_1$-$C_4$ alkyl and $R_6'$ is $CH_3$;
(2) when Q is SO, then W is O;
(3) when $R_4$ is other than H, then $R_5$ is H; and
(4) $R_1$ and $R_2$ taken together are not more than four carbon atoms.

2. Compounds of claim 1 of Formula I where W is O.

3. Compounds of claim 2 wherein $R_5$ is H, F, Cl, $CH_3$, $OCH_3$, $CO_2(C_1$-$C_2$ alkyl) or $SO_2(C_1$-$C_2$ alkyl), $R_4$ is H, Cl, $CH_3$ or $OCH_3$, Y is $CH_3$, $OCH_3$, $OC_2H_5$, $CH_2OCH_3$, $CH(OCH_3)_2$, $CF_3CH_2O$ or $OCF_2H$ and $R_{12}$ is H.

4. Compounds of claim 3 where $R_3$ and $R_4$ are H, $R_1$ is H, $CH_3$ or $CH_2CH_3$, $R_2$ is H or $CH_3$ and $R_5$ is H, F, Cl, $CH_3$ or $OCH_3$.

5. Compounds of claim 4 where Y is $CH_3$, $OCH_3$ or $CH_2OCH_3$.

6. Compounds of claim 1 of Formula II where W is O.

7. Compounds of claim 6 where $R_6$ is H, $CH_3$ or $CH_2CH_3$ and $R_6'$ is H.

8. Compounds of claim 7 where $R_5$ is H, Cl, $CH_3$, $OCH_3$, $CO_2(C_1$-$C_2$alkyl) or $SO_2(C_1$-$C_2$ alkyl), $R_4$ is H, Cl, $CH_3$ or $OCH_3$, Y is $CH_3$, $OCH_3$, $OC_2H_5$, $CH_2OCH_3$, $CH(OCH_3)_2$, $CF_3CH_2O$ or $OCF_2H$ and $R_{12}$ is H.

9. Compounds of claim 8 where $R_4$ and $R_6'$ are H, $R_5$ is H, F, Cl, $CH_3$ or $OCH_3$, and $R_6$ is H or $CH_3$.

10. Compounds of claim 9 where Y is $CH_3$, $OCH_3$ or $CH_2OCH_3$.

11. A composition suitable for controlling the growth of undesired vegetation which comprises an effective amount of a compound of claim 1 and at least one of the following: surfactant, solid or liquid diluent.

12. A composition suitable for controlling the growth of undesired vegetation which comprises an effective amount of a compound of claim 2 and at least one of the following: surfactant, solid or liquid diluent.

13. A composition suitable for controlling the growth of undesired vegetation which comprises an effective amount of a compound of claim 3 and at least one of the following: surfactant, solid or liquid diluent.

14. A composition suitable for controlling the growth of undesired vegetation which comprises an effective amount of a compound of claim 4 and at least one of the following: surfactant, solid or liquid diluent.

15. A composition suitable for controlling the growth of undesired vegetation which comprises an effective amount of a compound of claim 5 and at least one of the following: surfactant, solid or liquid diluent.

16. A composition suitable for controlling the growth of undesired vegetation which comprises an effective amount of a compound of claim 6 and at least one of the following: surfactant, solid or liquid diluent.

17. A composition suitable for controlling the growth of undesired vegetation which comprises an effective amount of a compound of claim 7 and at least one of the following: surfactant, solid or liquid diluent.

18. A composition suitable for controlling the growth of undesired vegetation which comprises an effective amount of a compound of claim 8 and at least one of the following: surfactant, solid, or liquid diluent.

19. A composition suitable for controlling the growth of undesired vegetation which comprises an effective amount of a compound of claim 9 and at least one of the following: surfactant, solid or liquid diluent.

20. A composition suitable for controlling the growth of undesired vegetation which comprises an effective amount of a compound of claim 10 and at least one of the following: surfactant, solid or liquid diluent.

21. A method for controlling the growth of undesired vegetation which comprises applying to the locus to be protected an effective amount of a compound of claim 1.

22. A method for controlling the growth of undesired vegetation which comprises applying to the locus to be protected an effective amount of a compound of claim 2.

23. A method for controlling the growth of undesired vegetation which comprises applying to the locus to be protected an effective amount of a compound of claim 3.

24. A method for controlling the growth of undesired vegetation which comprises applying to the locus to be protected an effective amount of a compound of claim 4.

25. A method for controlling the growth of undesired vegetation which comprises applying to the locus to be protected an effective amount of a compound of claim 5.

26. A method for controlling the growth of undesired vegetation which comprises applying to the locus to be protected an effective amount of a compound of claim 6.

27. A method for controlling the growth of undesired vegetation which comprises applying to the locus to be protected an effective amount of a compound of claim 7.

28. A method for controlling the growth of undesired vegetation which comprises applying to the locus to be protected an effective amount of a compound of claim 8.

29. A method for controlling the growth of undesired vegetation which comprises applying to the locus to be protected an effective amount of a compound of claim 9.

30. A method for controlling the growth of undesired vegetation which comprises applying to the locus to be protected an effective amount of a compound of claim 10.

* * * * *